(12) United States Patent
Onuki et al.

(10) Patent No.: US 12,257,557 B2
(45) Date of Patent: Mar. 25, 2025

(54) BONDED BODY, SEPARATION MEMBRANE MODULE EQUIPPED WITH SAME, AND METHOD FOR PRODUCING ALCOHOL

(71) Applicants: Mitsubishi Chemical Corporation, Tokyo (JP); JAPAN TECHNOLOGICAL RESEARCH ASSOCIATION OF ARTIFICIAL PHOTOSYNTHETIC CHEMICAL PROCESS, Tokyo (JP)

(72) Inventors: Masamichi Onuki, Tokyo (JP); Naoyuki Sakamoto, Tokyo (JP); Susumu Tsutsuminai, Tokyo (JP); Koetsu Endou, Tokyo (JP); Naoko Fujita, Tokyo (JP); Misa Hara, Tokyo (JP); Masahiro Kujime, Tokyo (JP); Nobuo Toratani, Tokyo (JP)

(73) Assignees: Mitsubishi Chemical Corporation, Tokyo (JP); JAPAN TECHNOLOGICAL RESEARCH ASSOCIATION OF ARTIFICIAL PHOTOSYNTHETIC CHEMICAL PROCESS, Tokyo (JP)

( * ) Notice: Subject to any disclaimer, the term of this patent is extended or adjusted under 35 U.S.C. 154(b) by 750 days.

(21) Appl. No.: 17/165,025

(22) Filed: Feb. 2, 2021

(65) Prior Publication Data
US 2021/0154623 A1    May 27, 2021

Related U.S. Application Data

(63) Continuation of application No. PCT/JP2019/030610, filed on Aug. 2, 2019.

(30) Foreign Application Priority Data

Aug. 2, 2018  (JP) ................. 2018-146305
Aug. 2, 2018  (JP) ................. 2018-146331
(Continued)

(51) Int. Cl.
*B01D 69/10*     (2006.01)
*B01D 71/02*     (2006.01)
(Continued)

(52) U.S. Cl.
CPC ........ *B01D 69/108* (2022.08); *B01D 71/024* (2013.01); *B01D 71/0281* (2022.08);
(Continued)

(58) Field of Classification Search
None
See application file for complete search history.

(56) References Cited

U.S. PATENT DOCUMENTS 5,518,530 A       5/1996  Sakai et al.
2005/0011358 A1   1/2005  Yamada et al.
(Continued)

FOREIGN PATENT DOCUMENTS

CA    2186222 A1    10/1995
JP    7-163827 A     6/1995
(Continued)

OTHER PUBLICATIONS

Japanese Office Action issued Jan. 10, 2023 in Japanese Application 2019-142136, (with unedited computer-generated English translation), 10 pages.
(Continued)

*Primary Examiner* — Jason M Greene
(74) *Attorney, Agent, or Firm* — Oblon, McClelland, Maier & Neustadt, L.L.P.

(57) ABSTRACT

The present invention addresses the problem of providing a bonded body which has a high airtightness and exhibits
(Continued)

excellent durability under high-temperature and high-pressure conditions. This problem is solved by a bonded body in which a complex of a zeolite and an inorganic porous support, and a dense member are bonded together by an inorganic glass or an inorganic adhesive. The inorganic glass or the inorganic adhesive has a thermal expansion coefficient of $30\times10^{-7}$/K to $90\times10^{-7}$/K, and the inorganic glass has a softening point of 550° C. or lower. The present invention also addresses the problem of providing a method of efficiently producing an alcohol by installing a separation membrane in an alcohol synthesis reactor based on a bonding method that gives good sealing performance and durability under high-temperature and high-pressure conditions and in the presence of methanol vapor. This problem can be solved by an alcohol production method of obtaining an alcohol by allowing a raw material gas, which contains at least hydrogen and carbon monoxide and/or carbon dioxide, to react in the presence of a catalyst in a reactor. In the reactor for carrying out the reaction, an alcohol-selective permeable membrane bonded with a dense member is installed, and an alcohol generated by the reaction permeates and is recovered through the selective permeable membrane.

15 Claims, 13 Drawing Sheets

(30) Foreign Application Priority Data

Aug. 2, 2018 (JP) .................................. 2018-146338
Sep. 3, 2018 (JP) .................................. 2018-164260

(51) Int. Cl.
  *C07C 29/152* (2006.01)
  *C07C 31/04* (2006.01)
(52) U.S. Cl.
  CPC .... *C07C 29/152* (2013.01); *B01D 2201/0415* (2013.01); *C07C 31/04* (2013.01)

(56) References Cited

U.S. PATENT DOCUMENTS

| | | | | |
|---|---|---|---|---|
| 2010/0298115 A1* | 11/2010 | Yajima | ................. | B01D 71/028 502/4 |
| 2011/0174722 A1* | 7/2011 | Yano | .................... | B01D 71/028 501/153 |
| 2016/0176775 A1 | 6/2016 | Gruetzner et al. | | |
| 2018/0029892 A1* | 2/2018 | Yu | ........................ | C01G 23/047 |
| 2019/0152885 A1 | 5/2019 | Kambe et al. | | |
| 2019/0218426 A1 | 7/2019 | Hatakeyama et al. | | |

FOREIGN PATENT DOCUMENTS

| | | | |
|---|---|---|---|
| JP | 9-511509 A | 11/1997 | |
| JP | 10-180060 A | 7/1998 | |
| JP | 2000-109690 A | 4/2000 | |
| JP | 2000-192221 A | 7/2000 | |
| JP | 2001-79398 A | 3/2001 | |
| JP | 2004-243246 A | 9/2004 | |
| JP | 2005-58950 A | 3/2005 | |
| JP | 2007-50322 A | 3/2007 | |
| JP | 2007-55970 A | 3/2007 | |
| JP | 2007-291440 A | 11/2007 | |
| JP | 2009-66528 A | 4/2009 | |
| JP | 2010-110704 A | 5/2010 | |
| JP | 2013-43170 A | 3/2013 | |
| JP | 2013-203602 * | 10/2013 | ............. C04B 37/02 |
| JP | 2013-203602 A | 10/2013 | |
| JP | 2015-20143 A | 2/2015 | |
| JP | 2016-52959 A | 4/2016 | |
| JP | 2016-117726 A | 6/2016 | |
| JP | 2016-174996 A | 10/2016 | |
| JP | 2016-175054 A | 10/2016 | |
| JP | 2016-193426 A | 11/2016 | |
| JP | 2018-8940 A | 1/2018 | |
| JP | 2018-24206 A | 2/2018 | |
| JP | 2018-56509 A | 4/2018 | |
| WO | WO 2009/113715 A1 | 9/2009 | |
| WO | WO 2010/099635 A1 | 9/2010 | |
| WO | WO 2017/175760 A1 | 10/2017 | |

OTHER PUBLICATIONS

Japanese Office Action issued Jan. 10, 2023 in Japanese Application 2019-142185, (with unedited computer-generated English translation), 8 pages.
Japanese Office Action issued Jan. 10, 2023 in Japanese Application 2019-154313, (with unedited computer-generated English translation), 8 pages.
Japanese Office Action issued Feb. 14, 2023 in Japanese Application 2019-142823, (with unedited computer-generated English translation), 6 pages.
Saudi Arabian Office Action issued Sep. 29, 2022 in Saudi Arabian Patent Application No. 521421150 (with English language translation), 16 pages.
Japanese Office Action issued on Jul. 25, 2023 in Japanese Patent Application No. 2019-142823 (with English translation), 6 pages.
International Search Report issued Oct. 21, 2019 in PCT/JP2019/030610 (submitting English translation only), 7 pages.
International Preliminary Report on Patentability and Written Opinion of the International Searching Authority issued on Feb. 11, 2021 in PCT/JP2019/030610 filed Aug. 2, 2019, (submitting English translation only), 22 pages.
Fausto Gallucci, et al., "An Experimental Study of $CO_2$ Hydrogenation into Methanol Involving a Zeolite Membrane Reactor" Chemical Engineering and Processing, vol. 43, Issue 8, 2004, pp. 1029-1036.
Józef Szarawara, et al., "Model Kinetyczny Niskocisnieniowej Sysntezy Metanolu" Inz. Chem. Proc., vol. 1, No. 2, 1980, pp. 331-343, (Including English Abstract).
K. M. Vanden Bussche, et al. "A Steady-State Kinetic Model for Methanol Synthesis and the Water Gas Shift Reaction on a Commercial $Cu/ZnO/Al_2O_3$ Catalyst" Journal of Catalysis, vol. 161, 1996, pp. 1-10.
The partial Supplementary European Search Report issued Aug. 3, 2021 in European Patent Application 19844683.3, 15 pages.
Saudi Arabian Office Action issued Sep. 7, 2023 in Saudi Arabian Patent Application No. 521421150 (with English language translation), 14 pages.
Office Action issued May 20, 2024, in corresponding Australian Patent Application No. 2019313973, 4pages.
Office Action dated Nov. 25, 2024 issued in corresponding EP Application No. 19844683.3.

* cited by examiner

BONDED BODY, SEPARATION MEMBRANE MODULE EQUIPPED WITH SAME, AND METHOD FOR PRODUCING ALCOHOL

CROSS REFERENCE TO RERATED APPLICATIONS

This is a continuation of International Application PCT/JP2019/030610, filed on Aug. 2, 2019, which is claiming priority of Japanese Patent Application No. 2018-146305, filed on Aug. 2, 2018, Japanese Patent Application No. 2018-146331, filed on Aug. 2, 2018, Japanese Patent Application No. 2018-146338, filed on Aug. 2, 2018, and Japanese Patent Application No. 2018-164240, filed on Sep. 3, 2018, the entire contents of which are incorporated herein by reference.

TECHNICAL FIELD

The present invention relates to a bonded body, a separation membrane module including the same, and a method of producing an alcohol, preferably methanol.

BACKGROUND ART

A membrane having a gas separation capability is usually formed on an inorganic porous support, and bonded to a gas impermeable dense member for use. In this case, it is necessary that the membrane and the dense member be bonded in a highly airtight state. When such a membrane having a gas separation capability is used for the purpose of checking its performance and the like in experimental gas separation rather than being installed in a reactor and used for industrial gas separation, an instant adhesive or the like may be used for the bonding since a bonded state needs to be maintained only for a short period; however, in those cases where the membrane is actually installed in a reactor and used for gas separation for a long time in a stable manner, a glass is often used for the bonding. Bonding with a glass has been commonly used industrially since it allows a separation membrane part to be easily removed by reheating for replacement. Patent Document 1 discloses a bonded body in which a gas separation membrane made of a metal is bonded to a metallic member with a glass having a thermal expansion coefficient of $50\times10^{-7}$/K to $80\times10^{-7}$/K. Further, Patent Document 2 discloses that a zeolite membrane and an alumina gas pipe can be bonded together using a separation membrane-sealing composition composed of alumina and a specific glass containing prescribed amounts of $B_2O_3$ and PbO. That is, thus far, a metallic member and a ceramic dense member have been generally used for a metallic separation membrane and a ceramic support, respectively, in view of the thermal expansion coefficient. Moreover, Patent Document 3 discloses a structure in which a ceramic member and an Fe—Ni—Co alloy member are sealed with a glass having a thermal expansion coefficient of $55\times10^{-7}$/K to $65\times10^{-7}$/K.

When a zeolite member is used as a membrane having a gas separation capability, a high-temperature treatment is not preferred because of a concern in the heat resistance of the zeolite membrane. Such a bonding treatment performed at a high temperature of 900° C. or higher as disclosed in Patent Documents 1 and 3 may deteriorate the structure of the zeolite, such as its breakage, and thereby reduce the separation performance thereof. In addition, not only does bonding at high-temperature require time for heating and cooling but also the bonding part itself will be damaged due to temperature changes, which affects the separation performance and the life of the resulting bonded body, and results in a reduction in the efficiency and an increase in the cost for mass production of the bonded body.

Meanwhile, a bonded body in which a separation membrane is bonded is required to have a sufficient airtightness and, at the same time, be usable for a long time while withstanding the use temperature and the use pressure. However, conventional bonded bodies do not satisfy these requirements. For example, the bonded body disclosed in Patent Document 2, in which a ceramic such as alumina is bonded to a separation membrane, does not have sufficient strength and durability. Particularly, when used for a long time under a high temperature and a high pressure, cracking occurs due to multiple factors such as vibration generated by contact with a fluid, and there are even cases where the bonded body is broken.

It is proposed to use a lead glass as a bonded body that not only has a sufficient airtightness but also is strong against temperature changes and can be used for a long time while withstanding the reaction pressure. For example, as disclosed in Patent Document 2, the use of such a glass containing PbO as a main component enables to adopt a firing temperature of 600° C. or lower. However, lead is known to cause chronic poisoning when accumulated in the body, and its use has an environmental problem and goes against the global trend of regulating the use of lead.

Moreover, when a swellable resin such as an epoxy resin is used as a bonding agent as disclosed in Patent Document 4, exposure of the bonding agent to an organic solvent under a high-temperature and high-pressure condition accelerates deterioration as shown below in Comparative Examples, resulting in breakage of the bonded body in some cases.

Methods of producing methanol from a gas containing hydrogen and carbon monoxide (hereinafter, referred to as "syngas") have been known for a long time, and examples thereof include a method that uses a copper-based catalyst (e.g., a copper-zinc-based catalyst or a copper-chromium-based catalyst).

The reaction for producing methanol from the syngas, which is an equilibrium reaction, is more advantageous at a lower temperature and a higher pressure. The rate of this reaction is reduced at a low temperature, and a general methanol production process is thus carried out under severe conditions of 200 to 300° C. and 5 to 10 MPaG (or even a higher pressure); therefore, this process consumes a great amount of energy during the methanol production and places many restrictions on equipment.

As methods for efficiently producing methanol, several methods in which a gas composition in a reactor is shifted from an equilibrium composition by removing methanol from the reaction system so as to carry out the reaction at a conversion rate higher than the equilibrium conversion rate have been proposed.

In addition, Patent Documents 5, 6, 7 and 8 propose methods for increasing the conversion rate to be higher than the equilibrium conversion rate by installing a separation membrane in a methanol synthesis reactor, and removing methanol and water from the reaction system using the separation membrane.

Further, Non-patent Document 1 reports a method in which a separation membrane sealed with a graphite packing is installed in a methanol reactor at a high temperature and a high pressure.

Non-patent Documents 2 and 3 report the temperature dependency and the pressure dependency of the rate of a methanol synthesis reaction without a separation membrane and the rate of a water-gas shift reaction occurring simultaneously.

RELATED ART DOCUMENTS

Patent Documents

[Patent Document 1] Japanese Unexamined Patent Application Publication No. H7-163827
[Patent Document 2] Japanese Unexamined Patent Application Publication No. H10-180060
[Patent Document 3] Japanese Unexamined Patent Application Publication No. 2013-203602
[Patent Document 4] Japanese Unexamined Patent Application Publication No. 2007-50322
[Patent Document 5] Japanese Unexamined Patent Application Publication (Translation of PCT Application) No. H9-511509
[Patent Document 6] Japanese Unexamined Patent Application Publication No. 2016-117726
[Patent Document 7] Japanese Unexamined Patent Application Publication No. 2016-174996
[Patent Document 8] Japanese Unexamined Patent Application Publication No. 2007-55970

Non-Patent Documents

[Non-patent Document 1] Chem. Eng. Process. 43 (2004), 1029
[Non-patent Document 2] Szarawara, J. Reychman, K. 1980. Inz Chem Proc., 1:331
[Non-patent Document 3] Vanden Bussche K. M., Froment G. F., 1996. J. Catal., 161, 1-10

SUMMARY OF THE INVENTION

Problems to be Solved by the Invention

An object of the present invention is to provide a bonded body in which a complex of a zeolite and an inorganic porous support is bonded to a dense member and, in this provision, not only to realize a high airtightness but also to attain excellent durability particularly under high-temperature and high-pressure conditions, while taking into consideration the environment by reducing the use of lead (first object).

Another object of the present invention is to provide a bonded body in which a complex of a zeolite and an inorganic porous support is bonded to a dense member and, in this provision, not only to realize a high airtightness and to substantially eliminate any damage to the zeolite during bonding, but also to attain excellent durability particularly under high-temperature and high-pressure conditions (second object).

Yet another object of the present invention is to provide a bonded body in which a complex of a zeolite and an inorganic porous support is bonded to a dense member and, in this provision, not only to realize a high airtightness by a simple method that does not require high-temperature firing and the like, but also to attain excellent durability such that the bonded body can be used for a long time particularly under high-temperature and high-pressure conditions and/or in the presence of a solvent and a gas, especially an organic solvent and an organic gas (third object).

In the methods proposed by Patent Documents 5, 6, 7 and 8 in which a separation membrane is installed in a methanol synthesis reactor, the gas supply side (high pressure) and the gas permeation side (low pressure) must be sealed for a long time under high-temperature and high-pressure conditions and in the presence of methanol vapor, and there is a problem in terms of the method of bonding the separation membrane to other members. However, Patent Documents 5, 6 and 7 do not disclose any concrete bonding methods or an example performed under high-temperature and high-pressure conditions.

Patent Document 8 describes examples in which water is removed from a methanol synthesis reactor using a separation membrane under high-temperature and high-pressure conditions of 200° C. and 3 MPaG; however, it also offers no description about a concrete bonding method, and the sealing performance and the durability are unclear.

The mechanical sealing method described in Non-patent Document 1, in which a graphite packing or the like is used, is not suitable for industrial use since it not only takes labor for locking membranes one by one in installing them but also requires a casing of the graphite packing, and this leads to an increase in the volume of a bonded part. In addition, the auxiliary agent used for molding graphite into the packing is not durable against methanol vapor and thus cannot be used for a long time.

The present invention was made under the above-described circumstances, and yet another object of the present invention is to provide a method of efficiently producing methanol by installing a separation membrane in a methanol synthesis reactor based on a bonding method that gives good sealing performance and durability under high-temperature and high-pressure conditions and in the presence of methanol vapor (fourth object).

In the present invention, as described above, by using a zeolite and the like as a separation membrane to remove a generated alcohol from a reactor, the yield can be dramatically improved. However, since the reaction for obtaining an alcohol is an intense exothermic reaction, the amount of generated heat is increased with the amount of the alcohol generated by the reaction, as a result of which the zeolite is damaged due to an increase in the temperature inside the reactor, and this leads to a reduction in the alcohol separation efficiency in some cases. In addition, an increase in the flow rate of raw materials causes an increase in the temperature inside the reactor, and such an increase in the temperature shifts the equilibrium reaction toward the side of the raw materials which are hydrogen and carbon monoxide and/or carbon dioxide. These points are also obstacle to obtain an alcohol in a more efficient manner.

Moreover, in a case where only a catalyst reaction is carried out without the removal of the generated alcohol from the reactor, the temperature inside the reactor is increased by the reaction heat, and the equilibrium is consequently shifted toward the raw material side and the alcohol-generating reaction is thereby inhibited; therefore, the increase in the temperature inside the reactor slows down and eventually peaks out at some point due to the equilibrium constraint. On the other hand, in a case where a catalyst reaction and the use of a separation membrane are combined, since the product is extracted out of the system, there is a new problem that the equilibrium constraint is weakened and the reaction temperature tends to be largely increased as a result.

Therefore, the present invention is also aimed at providing a production apparatus and a method, which can not only improve the yield but also reduce the energy required for the production of an alcohol by removing such generated reaction heat from a reactor and using this heat for, for example, heating hydrogen, carbon monoxide and/or carbon dioxide that are the raw materials (fifth object).

Means for Solving the Problems

The present inventors intensively studied to discover that the above-described problems can be solved by using an inorganic glass or an inorganic adhesive, which has a specific thermal expansion coefficient and a softening point, to bond a complex of a zeolite and an inorganic porous support to a dense member in a just enough manner, thereby reaching the present invention.

Further, the present inventors discovered that the above-described problems can be solved by installing a methanol-selective permeable membrane, which is bonded to a dense member using a specific bonding material, in a reactor when producing methanol from a raw material gas containing hydrogen and carbon monoxide and/or carbon dioxide, thereby completing the present invention.

The first embodiment of the present invention includes the followings.
- [A1-1] A bonded body in which a complex of a zeolite and an inorganic porous support, and a dense member are bonded together with a lead-free inorganic glass, wherein the lead-free inorganic glass has a thermal expansion coefficient of $30 \times 10^{-7}$/K or more and $90 \times 10^{-7}$/K or less and a softening point of 550° C. or lower.
- [A1-2] The bonded body according to [A1-1], wherein a bonded part between the complex and the dense member is covered with a sealing film.
- [A1-3] The bonded body according to [A1-2], wherein the sealing film is a silica film.
- [A1-4] The bonded body according to any one of [A1-1] to [A1-3], wherein the lead-free inorganic glass contains SnO and/or $B_2O_3$.
- [A1-5] The bonded body according to any one of [A1-1] to [A1-4], wherein the dense member has a thermal expansion coefficient of $30 \times 10^{-7}$/K to $200 \times 10^{-7}$/K.
- [A1-6] A method of using a bonded body, in which the bonded body according to any one of [A1-1] to [A1-5] is used under a high-temperature condition of 100° C. to 500° C. and/or a high-pressure condition of 0.5 to 10 MPa.
- [A1-7] A separation membrane module, including the bonded body according to any one of [A1-1] to [A1-6].
- [A1-8] A reactor, including the separation membrane module according to [A1-7].
- [A1-9] A bonding method for bonding a complex of a zeolite and an inorganic porous support to a dense member using a lead-free inorganic glass, wherein the lead-free inorganic glass has a thermal expansion coefficient of $30 \times 10^{-7}$/K or more and $90 \times 10^{-7}$/K or less, and a softening point of 550° C. or lower.

The second embodiment of the present invention includes the followings.
- [A2-1] A bonded body in which a complex of a zeolite and an inorganic porous support, and a dense member are bonded together with an inorganic glass, wherein the dense member is a metal member, and the inorganic glass has a thermal expansion coefficient of $30 \times 10^{-7}$/K or more and $90 \times 10^{-7}$/K or less, and a softening point of 550° C. or lower.
- [A2-2] The bonded body according to [A2-1], wherein a bonded part between the complex and the dense member is covered with a sealing film.
- [A2-3] The bonded body according to [A2-2], wherein the sealing film is a silica film.
- [A2-4] The bonded body according to any one of [A2-1] to [A2-3], wherein the inorganic glass contains SnO and/or $B_2O_3$.
- [A2-5] The bonded body according to any one of [A2-1] to [A2-4], wherein the dense member has a thermal expansion coefficient of $30 \times 10^{-7}$/K or more and $200 \times 10^{-7}$/K or less.
- [A2-6] A method of using a bonded body, in which the bonded body according to any one of [A2-1] to [A2-5] is used under a high-temperature condition of 100° C. to 500° C. and/or a high-pressure condition of 0.5 to 10 MPa.
- [A2-7] A separation membrane module, including the bonded body according to any one of [A2-1] to [A2-5].
- [A2-8] A reactor, including the separation membrane module according to [A2-7].
- [A2-9] A bonding method for bonding a complex of a zeolite and an inorganic porous support to a dense member using an inorganic glass, wherein the dense member is a metal member, and the inorganic glass has a thermal expansion coefficient of $30 \times 10^{-7}$/K or more and $90 \times 10^{-7}$/K or less, and a softening point of 550° C. or lower.

The third embodiment of the present invention includes the followings.
- [B1] A bonded body in which a complex of a zeolite and an inorganic porous support, and a dense member are bonded together with an inorganic adhesive having a post-curing thermal expansion coefficient of $30 \times 10^{-7}$/K to $90 \times 10^{-7}$/K.
- [B2] A bonded body in which a complex of a zeolite and an inorganic porous support, and a dense member are bonded together with an inorganic adhesive, wherein a difference in thermal expansion coefficient between the dense member and the inorganic adhesive after cured is $50 \times 10^{7}$/K.
- [B3] The bonded body according to [B1] or [B2], wherein the inorganic adhesive contains a metal alkoxide.
- [B4] The bonded body according to any one of [B1] to [B3], wherein a bonded part between the complex and the dense member is covered with a sealing film.
- [B5] The bonded body according to [B4], wherein the sealing film is a silica film.
- [B6] The bonded body according to any one of [B1] to [B5], wherein the dense member has a thermal expansion coefficient of $30 \times 10^{-7}$/K to $200 \times 10^{-7}$/K.
- [B7] A method of using a bonded body, in which the bonded body according to any one of [B1] to [B6] is used under a high-temperature condition of 100° C. to 500° C. and/or a high-pressure condition of 0.5 to 10 MPa.
- [B8] A separation membrane module including the bonded body according to any one of [B1] to [B6].
- [B9] A reactor including the separation membrane module according to [B8].
- [B10] A bonding method for bonding a complex of a zeolite and an inorganic porous support to a dense member using an inorganic adhesive having a post-curing thermal expansion coefficient of $30 \times 10^{-7}$/K to $90 \times 10^{-7}$/K.

The fourth embodiment of the present invention includes the followings.
- [C1-1] A methanol production method for obtaining methanol by allowing a raw material gas, which contains at least hydrogen and carbon monoxide and/or carbon dioxide, to react in the presence of a catalyst in a reactor, wherein, in the reactor for carrying out the reaction, a methanol-selective permeable membrane, which is bonded to a dense member with a bonding material containing an inorganic oxide as a main component and having a linear expansion coefficient of $30\times10^{-7}$/K or more and $90\times10^{-7}$/K or less, is installed, and methanol generated by the reaction permeates through the selective permeable membrane and is recovered.

[C1-2] The methanol production method according to [C1-1], wherein the methanol-selective permeable membrane is a zeolite membrane.

[C1-3] The methanol production method according to [C1-1] or [C1-2], wherein the dense member is made of a metal.

[C1-4] The methanol production method according to any one of [C1-1] to [C1-3], wherein, in the reactor, the methanol partial pressure on a gas supply side of the methanol-selective permeable membrane is 0.1 MPa or more and 6 MPa or less.

[C1-5] The methanol production method according to any one of [C1-1] to [C1-4], wherein the temperature inside the reactor is 200° C. or higher and 300° C. or lower.

[C1-6] The methanol production method according to any one of [C1-1] to [C1-5], wherein, in the reactor, the pressure on the gas supply side of the methanol-selective permeable membrane is 1 MPaG or more and 8 MPaG or less.

[C1-7] The methanol production method according to any one of [C1-1] to [C1-6], wherein the dense member has a linear expansion coefficient of $30\times10^{-7}$/K or more and $200\times10^{-7}$/K or less.

[C1-8] The methanol production method according to any one of [C1-1] to [C1-7], wherein the dense member is made of kovar.

[C1-9] The methanol production method according to any one of [C1-1] to [C1-8], wherein the inorganic oxide is an inorganic glass or an inorganic adhesive.

[C1-10] A methanol production apparatus used for a method of producing methanol by allowing a raw material gas, which contains at least hydrogen and carbon monoxide and/or carbon dioxide, to react in the presence of a catalyst in a reactor, wherein the methanol production apparatus has a structure in which, in the reactor for carrying out the reaction, a methanol-selective permeable membrane, which is bonded to a dense member with a bonding material containing an inorganic oxide as a main component and having a linear expansion coefficient of $30\times10^{-7}$/K or more and $90\times10^{-7}$/K or less, is installed, and methanol generated by the reaction permeates through the selective permeable membrane and is recovered.

The fourth embodiment of the present invention further includes the followings.

[C2-1] A methanol production method for obtaining methanol by allowing a raw material gas, which contains at least hydrogen and carbon monoxide and/or carbon dioxide, to react in the presence of a catalyst in a reactor, wherein, in the reactor for carrying out the reaction, a methanol-selective permeable membrane is installed, and methanol generated by the reaction permeates through the selective permeable membrane and is recovered.

[C2-2] The methanol production method according to [C2-1], wherein the catalyst exists adjacent to the methanol-selective permeable membrane.

[C2-3] A methanol production apparatus used for a method of producing methanol by allowing a raw material gas, which contains at least hydrogen and carbon monoxide and/or carbon dioxide, to react in the presence of a catalyst in a reactor, wherein the methanol production apparatus has a structure in which, in the reactor for carrying out the reaction, a methanol-selective permeable membrane is installed, and methanol generated by the reaction permeates through the selective permeable membrane and is recovered.

[C2-4] The methanol production apparatus according to [C2-3], wherein the catalyst exists adjacent to the methanol-selective permeable membrane.

The fifth embodiment of the present invention includes the followings.

[D1] An alcohol production apparatus for synthesizing an alcohol by allowing raw materials, which contain at least hydrogen and carbon monoxide and/or carbon dioxide, to react in the presence of a catalyst, wherein the production apparatus includes: a reactor equipped with a zeolite-containing alcohol-selective permeable membrane; heat recovery means for recovering at least some of reaction heat from the reactor; and heat supply means for supplying the heat recovered by the heat recovery means.

[D2] The alcohol production apparatus according to [D1], wherein the heat recovery means is a heat exchanger, and the heat exchanger is provided in or adjacent to the reactor.

[D3] The alcohol production apparatus according to [D1] or [D2], wherein the heat supply means is a heat exchanger.

[D4] The alcohol production apparatus according to any one of [D1] to [D3], wherein the alcohol-selective permeable membrane has a permeability coefficient ratio of methanol/hydrogen of 10 or higher.

[D5] An alcohol production method, including a synthesis step of synthesizing an alcohol by allowing raw materials, which contain at least hydrogen and carbon monoxide and/or carbon dioxide, to react in the presence of a catalyst, wherein the alcohol production method further includes: a separation-recovery step of separating and recovering the thus obtained alcohol in a reactor using a zeolite-containing alcohol-selective permeable membrane; and a heat recovery step of recovering at least some of reaction heat generated in the synthesis step from the reactor, and a separation-recovery step and the heat recovery step are carried out concurrently.

[D6] The alcohol production method according to [D5], wherein, in the synthesis step, the temperature in the reactor is controlled at 200° C. or higher and 300° C. or lower.

[D7] The alcohol production method according to [D5] or [D6], further including a supply step of supplying at least some of the reaction heat recovered in the heat recovery step for heating at least one raw material selected from hydrogen, carbon monoxide and carbon dioxide before the raw material is introduced to the reactor.

[D8] The alcohol production method according to any one of [D5] to [D7], wherein a ratio of the area of the alcohol-selective permeable membrane with respect to the volume of the catalyst is 5 m$^2$/m$^3$ or more and 150 m$^2$/m$^3$ or less.

Effects of the Invention

According to the first embodiment of the present invention, in the production of a bonded body from a complex of a zeolite and an inorganic porous support, which is a separation membrane, and a dense member, a high airtightness can be realized while taking into consideration the environment by using a lead-free inorganic glass for bonding, and a bonded body which has excellent durability particularly under high-temperature and high-pressure conditions can be provided.

Further, according to the second embodiment of the present invention, in the production of a bonded body from a complex of a zeolite and an inorganic porous support, which is a separation membrane, and a dense member, by using a metal member as the dense member and a specific inorganic glass as a glass-based adhesive, the damage to the zeolite during bonding can be reduced, and a bonded body which has a high airtightness and exhibits a sufficient durability under high-temperature and high-pressure conditions can be provided.

Still further, according to third embodiment of the present invention, in the production of a bonded body from a complex of a zeolite and an inorganic porous support, which is a separation membrane, and a dense member, by employing a simple method that does not require high-temperature firing or the like, not only a bonded body of a complex of a zeolite and an inorganic porous support and a dense member, which bonded body has a high airtightness and can be used for a long time under high-temperature and high-pressure conditions and/or in the presence of a solvent and a gas, particularly an organic solvent and an organic gas, but also a separation membrane module including the bonded body can be provided.

Yet still further, according to the fourth embodiment of the present invention, a method of efficiently producing methanol by, for the production of methanol, installing a separation membrane in a methanol synthesis reactor based on a bonding method that gives good sealing performance and durability under high-temperature and high-pressure conditions and in the presence of methanol vapor, and allowing methanol generated by a reaction to permeate through the selective permeable membrane and be recovered, can be provided.

Furthermore, according to the fifth embodiment of the present invention, since the temperature in the reactor is not excessively increased, the damage to the zeolite is limited, so that the separation capacity of the zeolite membrane can be maintained for a long time. In addition, since the amount of alcohol generated by this equilibrium reaction is reduced at a high temperature, the yield can be maintained by preventing the temperature from excessively increasing in the reactor. Moreover, raw materials, which are hydrogen, carbon monoxide and/or carbon dioxide, need to be heated to a certain extent before being supplied to a catalyst. In a preferred mode, an alcohol production apparatus and an alcohol production method, in which the energy efficiency of the entire system can be improved by supplying recovered heat to the raw materials, can be provided.

MODE FOR CARRYING OUT THE INVENTION

Figure 1:
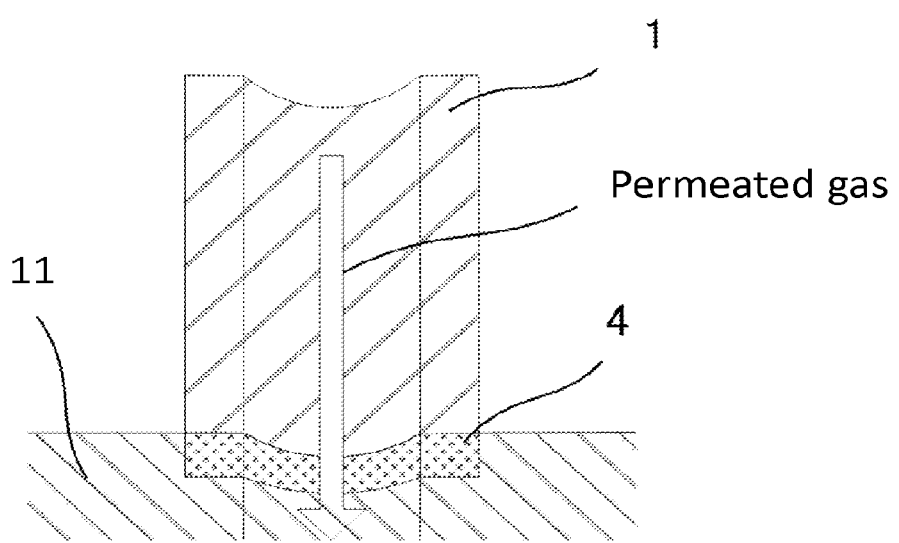
FIG. 1 is a schematic cross-sectional view of a bonded body in which a complex of a zeolite and an inorganic porous support is bonded to a dense member using an inorganic glass or an inorganic adhesive.

The present invention will now be described in detail; however, the following descriptions of the requirements are merely examples (representative examples) of the embodiments of the present invention, and the present invention is not limited to the contents thereof, and can be carried out with various modifications within the scope of the gist of present invention.

First Embodiment

The first embodiment of the present invention is a bonded body in which a complex of a zeolite and an inorganic porous support, and a dense member are bonded together with a lead-free inorganic glass, wherein the lead-free inorganic glass has a thermal expansion coefficient of $30 \times 10^{-7}$/K or more and $90 \times 10^{-7}$/K or less and a softening point of 550° C. or lower.

<Lead-Free Inorganic Glass>

In the present embodiment, the term "lead-free inorganic glass" refers to an inorganic glass having a lead (Pb) content of 10% by mass or less, preferably 5% by mass or less, more preferably 3% by mass or less, still more preferably 2% by mass or less, particularly preferably 1% by mass or less, most preferably 0% by mass, in terms of PbO.

The lead-free inorganic glass according to the present embodiment has a thermal expansion coefficient of usually $30 \times 10^{-7}$/K or higher, preferably $40 \times 10^{-7}$/K or higher, more preferably 45×10$^{-7}$/K or higher, but usually 90×10$^{-7}$/K or lower, preferably 80×10$^{-7}$/K or lower, more preferably 75×10$^{-7}$/K or lower.

In the present embodiment, the thermal expansion coefficient of the lead-free inorganic glass is usually 60% or more, preferably 70% or more, more preferably 80% or more, but usually 200% or less, preferably 150% or less, more preferably 120% or less, with respect to the thermal expansion coefficient of the dense member. With the thermal expansion coefficient of the lead-free inorganic glass being not higher than the above-described upper limit value, when bonding is performed at a temperature at which the lead-free inorganic glass is melted and the temperature is subsequently lowered, a tensile stress is unlikely to be generated inside the resulting bonded part, so that cracking of the bonded part is inhibited. Meanwhile, with the thermal expansion coefficient of the glass being not lower than the above-described lower limit value, a gap is unlikely to be generated between the complex and the dense member in the range of use temperature of the bonded body, so that a gas to be separated can be prevented from leaking through the gap to the purified gas side.

The bonded body obtained in this manner has a post-bonding air permeation amount of preferably 10 sccm or less, more preferably 8 sccm or less, most preferably 5 sccm or less, as determined by the test method described below in the section of Examples of the present specification.

Further, even when the air permeation amount is measured again after the post-bonding bonded body is heated in an autoclave to 280° C. by 1 hour with an addition of 1/16 of methanol and 1/16 of desalted water by volume with respect to the inner volume of the autoclave, maintained in this state for 48 hours, subsequently naturally cooled and then dried at 120° C. for 4 hours under normal pressure, the air permeation amount is preferably 10 sccm or less, more preferably 8 sccm or less, most preferably 5 sccm or less. This requirement is preferred to be satisfied in addition to the requirement of the thermal expansion coefficient, since this prevents a problem in a bonded part even when methanol production is carried out for a longer time.

In the industrial use of a separation module including the bonded body of the present embodiment, the separation module may be subjected to reciprocal changes between room temperature and its use temperature, and may be operated at the use temperature for a long time. Therefore, the bonded part formed by the lead-free inorganic glass is required not to have leakage of a gas to be separated even under such high-temperature and high-pressure conditions, and the leakage of a gas to be separated can be inhibited by setting the thermal expansion coefficient of the lead-free inorganic glass in the above-described range.

The lead-free inorganic glass according to the present embodiment has a softening point of 550° C. or lower, preferably 530° C. or lower, more preferably 480° C. or lower. Generally speaking, a frit of a lead-free inorganic glass can be made to flow by firing at a temperature of about 50° C. higher than its softening point. Accordingly, by controlling the softening point of the lead-free inorganic glass in the above-described range, not only the zeolite and the lead-free inorganic glass can be chemically bound at a relatively low temperature of about 600° C. or lower but also the lead-free inorganic glass is allowed to flow into pores of the complex, whereby the complex and the dense member can be mechanically and firmly bonded together. In addition, by setting the bonding temperature to be relatively low, damage to the zeolite caused by heating during bonding can be reduced.

The lead-free inorganic glass is not particularly restricted as long as it has the above-described thermal expansion coefficient and softening point. Examples of a component contained in the lead-free inorganic glass include $SiO_2$, $Al_2O_3$, ZnO, $P_2O_5$, $Bi_2O_3$, BaO, $TiO_2$, $TeO_2$, $V_2O_5$, $B_2O_3$, and SnO. Thereamong, from the standpoint of improving the sealing performance, the lead-free inorganic glass particularly preferably contains $B_2O_3$ and/or SnO. Specific examples of the lead-free inorganic glass containing $B_2O_3$ and/or SnO include an SnO—$P_2O_5$ glass, a $Bi_2O_3$—ZnO glass, a $Bi_2O_3$—$B_2O_3$ glass, a $Bi_2O_3$—$B_2O_3$—$SiO_2$ glass, and a $Bi_2O_3$—ZnO—$B_2O_3$ glass. Examples of a commercially available product of a glass frit of such a lead-free inorganic glass include: "FP-74", "KP312E", "FP-67", "BNL115BB", "ASF-1094", "ASF-1098", and "ASF-1109" (which are manufactured by AGC Inc.), and "BF-0606" and "BF-0901" (which are manufactured by Nippon Electric Glass Co., Ltd.).

When the lead-free inorganic glass contains SnO, the content thereof is not particularly restricted; however, it is usually 80% by mass or less, preferably 75% by mass or less, more preferably 70% by mass or less, but usually 10% by mass or higher, preferably 20% by mass or higher, more preferably 30% by mass or higher.

By controlling the SnO content in this range, the fluidity of the glass is sufficiently maintained, so that sufficient sealing performance is likely to be attained. The details of the effect of adding SnO are not clear; however, SnO is known to function as a reductant, and it is presumed that SnO modifies an oxide film on the surface of the dense member and inhibits an increase in the thickness of the oxide film during a bonding treatment, consequently improving the sealing performance.

Meanwhile, when the lead-free inorganic glass contains $B_2O_3$, the content thereof is usually 25% by mass or less, preferably 20% by mass or less, more preferably 18% by mass or less, still more preferably 15% by mass or less, but usually 1% by mass or higher, preferably 2% by mass or higher, more preferably 3% by mass or higher.

An addition of $B_2O_3$ improves the wettability of the lead-free inorganic glass with the dense member, so that the sealing performance is likely to be improved. However, when the $B_2O_3$ content is high, the softening point tends to be increased and the choice of other component is to be limited for controlling the softening point to be 550° C. or lower; therefore, the $B_2O_3$ content is preferably selected to be in the above-described range. Further, since $B_2O_3$ is soluble in water and alcohols, the $B_2O_3$ content is preferably not higher than the above-described upper limit value when the lead-free inorganic glass has a chance of being exposed to such substances.

Examples of a method of quantifying the SnO content and the $B_2O_3$ content include an XRF (fluorescent X-ray analysis) method and an ICP (inductively-coupled plasma emission spectroscopy) method.

The form of the lead-free inorganic glass is not particularly restricted, and the lead-free inorganic glass can be used in the form of, for example, a powder glass frit, a tablet obtained by molding a glass fit by a tablet molding method or the like, a tablet obtained as a molded product by sintering a glass frit, or a glass paste obtained by uniformly dispersing a glass fit in an organic solvent or a binder. For the mass production of the bonded body, the lead-free inorganic glass is particularly preferably in the form of a tablet or a paste among the above-exemplified forms, since this leads to an improvement in the production efficiency.

<Zeolite>

A zeolite mainly constituting a zeolite membrane is preferably one which contains a zeolite having a pore structure of 6- to 12-membered oxygen ring, more preferably one which contains a zeolite having a pore structure of 6- to 10-membered oxygen ring.

The value n of the above-described zeolite having an n-membered oxygen ring indicates the number of oxygen atoms in a pore having the largest number of oxygen atoms among the pores formed by oxygen constituting a zeolite skeleton and T elements (elements other than oxygen constituting the skeleton). For example, when pores of 12-membered oxygen rings and pores of 8-membered rings exist as in the case of an MOR-type zeolite, the zeolite is considered to have a 12-membered oxygen ring.

Examples of the zeolite having a pore structure of 6- to 12-membered oxygen ring include, in terms of the codes defined by the International Zeolite Association (IZA): AEI, AEL, AFI, AFG, ANA, ATO, BEA, BRE, CAS, CDO, CHA, CON, DDR, DOH, EAB, EPI, ERI, ESV, EUO, FAR, FAU, FER, FRA, HEU, GIS, GIU, GME, GOO, ITE, KFI, LEV, LIO, LOS, LTA, LTL, LTN, MAR, MEP, MER, MEL, MFI, MON, MOR, MSO, MTF, MTN, MTW, MWW, NON, NES, OFF, PAU, PHI, RHO, RTE, RTH, RUT, SGT, SOD, STI, STT, TOL, TON, TSC, UFI, VNI, WEI, and YUG. The zeolite is preferably any one selected from these zeolites.

Further, the bonded body according to the present invention is preferably able to selectively adsorb a target substance by the zeolite for the purpose of, for example, allowing large-sized molecules to permeate therethrough or separating molecules of comparable sizes from one another, rather than as a simple molecular sieve, namely for the purpose of allowing molecules to permeate therethrough, simply based on molecular size differences. In other words, the bonded body according to the present invention is more preferably one which separates a target substance by selective adsorption thereof to the zeolite surface. The selective adsorption capacity of such zeolite is decreased when the use temperature is excessively high, and the effects of the present invention are thus more prominently exerted under a temperature condition of, for example, about 500° C. or lower.

<Inorganic Porous Support>

A zeolite is poor in plasticity; therefore, when it is made into a membrane, the membrane is produced in the form of being supported on a substrate. A support is a porous such that gas molecules can penetrate thereinto and, for example, the support has a large number of three-dimensionally continuous fine small holes.

In the present embodiment, a material constituting the support is preferably chemically stable enough not to react with a gas to be treated, and preferably has excellent mechanical strength. Specifically, various oxide ceramics, such as alumina, silica, silica-alumina, mullite, cordierite and zirconia, as well as silicon carbide, carbon, glass and the like can be used.

Further, the shape of the support varies depending on the intended use of the zeolite membrane; however, particularly, a zeolite membrane on a cylindrical support is strong against a pressure from the outside, and is thus suitable for the simple use in a batch process, a circulation process (including a recycle process), and the like.

<Complex of Zeolite and Inorganic Porous Support>

In the present embodiment, for example, a cylindrical support is prepared and, first, zeolite microcrystals are supported inside its pores. As a supporting method, for example, a dipping method, a rubbing method, a suction method, or an impregnation method can be employed. The microcrystals, which play a role as nuclei for the growth of crystals constituting a zeolite membrane, are also referred to as "seed crystals". For this zeolite growth process, hydrothermal synthesis can be employed in the same manner as in the zeolite synthesis. The thickness of the zeolite membrane in a zeolite membrane complex is not particularly restricted; however, it is usually 0.1 µm or greater, preferably 0.5 µm or greater, but usually 50 µm or less, preferably 20 µm or less. By controlling the zeolite membrane to have an appropriate thickness, the denseness is maintained, so that the selectivity of the membrane can be maintained high. In addition, a gas to be removed is allowed to sufficiently permeate through the membrane without increasing the pressure more than necessary.

Further, when the support has a tubular shape, the surface to be covered by zeolite may be the outside of the pipe, the inside of the pipe, or both thereof.

The steps up to growing zeolite crystals on the support can be carried out by a batch process with both ends of the support being left open.

<Dense Member>

The dense member is a member which has a denseness (airtightness) at a level that a gas used for a reaction and a reacted gas do not leak from the member. The dense member is not particularly restricted as long as it has such a denseness, and a metal is typically used. Examples of the metal include: SUS pipes made of stainless steel; ceramics, such as alumina and zirconia; and alloys, such as kovar.

The thermal expansion coefficient of the dense member is usually $30 \times 10^{-7}$/K or more and $200 \times 10^{-7}$/K or less, and a lower limit thereof is preferably $35 \times 10^{-7}$/K or higher, more preferably $40 \times 10^{-7}$/K or higher, still more preferably $45 \times 10^{-7}$/K or higher. An upper limit is preferably $150 \times 10^{-7}$/K or lower, more preferably $120 \times 10^{-7}$/K or lower, still more preferably $85 \times 10^{-7}$/K or lower. When the thermal expansion coefficient of the dense member is in this range, a difference thereof from the thermal expansion coefficient of the lead-free inorganic glass is small, so that good sealing performance and durability can be maintained.

It is noted here that, in the present invention, the term "thermal expansion coefficient" means a linear expansion coefficient, and indicates a rate of change of a solid in the lengthwise direction that is caused by an increase in the temperature. The thermal expansion coefficient can be measured in accordance with the method described in JIS Z2285 (Metallic Materials), JIS R1618 (Ceramics), or the like. The thermal expansion coefficient may be measured in a range where the change in thermal expansion length is linearly proportional to the change in temperature and, in the present specification, the thermal expansion coefficient is usually a value measured at 30 to 250° C.

<Bonded Body of Complex of Zeolite and Inorganic Porous Support, and Dense Member>

In the present embodiment, when the complex is a cylindrical support, both ends thereof may be bonded. For example, in the case of performing a mixed gas separation process using a zeolite membrane in which the complex is cylindrical, the outside of the cylindrical support having the zeolite membrane is filled with the mixed gas, and a pressure is applied thereto or the inside is vacuum-evacuated to execute separation. Accordingly, one end of the support may be sealed with a cap while the other end may be connected to a pipe, or both ends may be connected to a pipe.

As a method of bonding the complex having a zeolite membrane on its surface with a cap made of the dense member or with a pipe made of the dense member that has an end structure similar to that of a cap, any method may be employed as long as the complex and the cap can be bonded with the lead-free inorganic glass, and examples thereof include a method in which the lead-free inorganic glass is filled into a recess of the dense member, the complex having a zeolite membrane on its surface is placed thereon, and the dense member and the complex are subsequently fired under weighed by a weight placed on top of the complex and thereby bonded.

It is indispensable that the firing temperature for bonding the complex and the dense member using the lead-free inorganic glass is not lower than the softening point of the lead-free inorganic glass in use. Accordingly, the firing temperature is usually at least 10° C. higher than the softening point, preferably at least 30° C. higher than the softening point, more preferably at least 50° C. higher than the softening point. In order to avoid a thermal damage to the zeolite membrane, the firing temperature is usually 600° C. or lower, preferably 580° C. or lower, more preferably 560° C. or lower. Further, the firing time for the bonding is usually 5 minutes to 90 minutes, preferably 10 minutes or longer, more preferably 20 minutes or longer, but preferably 60 minutes or shorter, more preferably 40 minutes or shorter, after reaching the firing temperature.

Examples in which a complex of a zeolite and an inorganic porous support is bonded to a dense member with a lead-free inorganic glass, will now be described referring to FIGS. 1 to 3.

As illustrated in FIG. 1, a complex 1 of a zeolite and an inorganic porous support can be directly bonded to a flange 11 with a lead-free inorganic glass 4. In this mode, the risks of gas leakage and the like that are associated with deterioration of the connection between members over time can be reduced. In this case, the flange 11 is a dense member.

Figure 2:
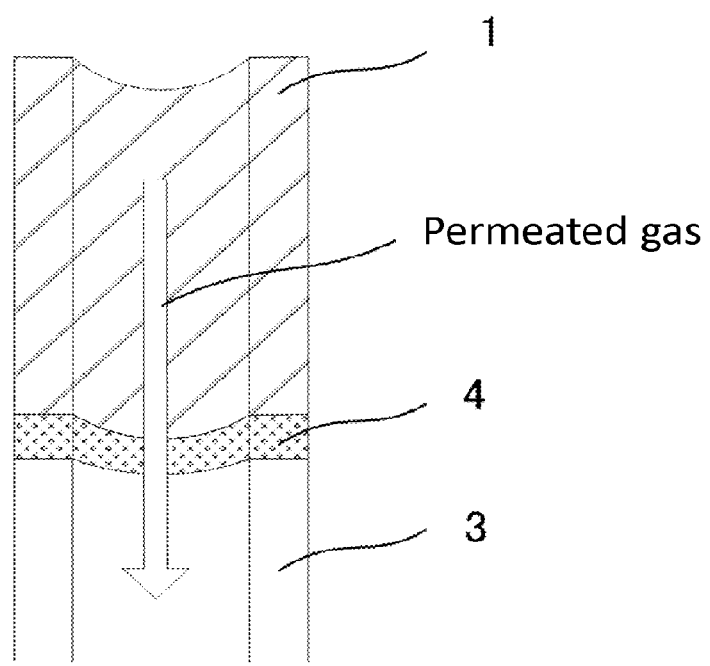
FIG. 2 is a schematic cross-sectional view of another bonded body in which a complex of a zeolite and an inorganic porous support is bonded to a dense member using an inorganic glass or an inorganic adhesive.

Meanwhile, as illustrated in FIG. 2, the complex 1 of a zeolite and an inorganic porous support may be simply bonded to a pipe 3 with the lead-free inorganic glass 4. Such bonding is also feasible since the lead-free inorganic glass of the present embodiment has high airtightness and durability. In this case, the pipe 3 is a dense member.

Figure 3:
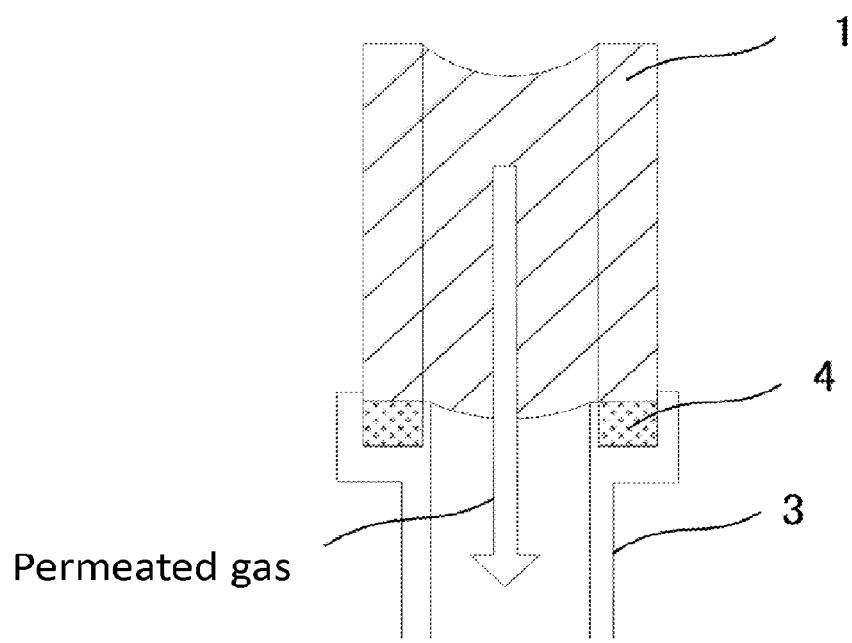
FIG. 3 is a schematic cross-sectional view of yet another bonded body in which a complex of a zeolite and an inorganic porous support is bonded to a dense member using an inorganic glass or an inorganic adhesive.

FIG. 3 is a schematic cross-sectional view that illustrates one example in which the complex 1 of a zeolite and an inorganic porous support, and the pipe 3 are bonded with the lead-free inorganic glass 4. The complex 1 of a zeolite and an inorganic porous support is bonded to the pipe 3 with the lead-free inorganic glass 4. The pipe 3 is bonded in such a manner to cover the complex 1 of a zeolite and an inorganic porous support.

It is noted here that the term "bonded body" used in the present invention refers to a component in which a complex of a zeolite and an inorganic porous support is bonded to a dense member and which is detachable for replacement when the performance of the complex is deteriorated. In cases where the bonded body does not have such a detachable mechanism, such as a case where the bonded body is integrated into a methanol synthesis reactor or the like, the bonded body also includes the dense member existing inside the reactor.

<Sealing Film>

In the present embodiment, a bonded part between the complex and the dense member is preferably covered with a sealing film. Due to the firing performed for curing the lead-free inorganic glass used for bonding, micropores such as microcracks and pinholes are formed on the surface of the bonded part in some cases. Therefore, from the standpoint of improving the sealing performance, it is preferred to seal these micropores by performing a sealing treatment on the bonded part. In addition, from the standpoints of inhibiting deterioration of the bonded part and damage to the pinholes and the like, it is desirable that the bonded part be covered with a sealing film formed by the sealing treatment.

Examples of a sealant that can form the sealing film include: various inorganic materials, such as silica and alumina; organic polymers, such as silicone resins, epoxy resins, and fluorine resins, and the sealant may contain a solvent or may be solvent-free. In the present embodiment, from the standpoints of the adhesion with the lead-free inorganic glass and the gas barrier performance, it is preferred to use an inorganic sealant, particularly silica. Further, from the standpoint of forming a dense film, it is also suitable to use a silicone resin. The amount of the sealant to be adhered may be decided as appropriate in accordance with the thickness of the desired sealing film.

From the standpoint of the ease of handing of the sealant, particularly inhibition of dripping, the viscosity of the sealant is preferably 2 (mPa·s, 25° C.) or higher, more preferably 5 (mPa·s, 25° C.) or higher, still more preferably 10 (mPa·s, 25° C.) or higher. Further, from the standpoint of allowing the sealant to permeate into the holes, the viscosity is 200 (mPa·s, 25° C.) or lower, preferably 100 (mPa·s, 25° C.) or lower, more preferably 50 (mPa·s, 25° C.) or lower. By controlling the viscosity in this range, the sealing performance (airtightness) is improved, and excellent ease of handling is attained.

As a specific method of the sealing treatment, first, the sealant is adhered to the bonded part by coating, spraying or the like to obtain a coating film. In this process, for the purpose of improving the sealing performance (airtightness), the pressure may be reduced on the side of the bonded part that is opposite to the side to which the sealant is adhered. This pressure reduction may be performed before, simultaneously with, or after adhering the sealant to the surface of the bonded body. By this pressure reduction, the sealant is allowed to permeate into the pores of the bonded part without any gaps, so that the pores on the surface of the bonded part can be sealed.

Subsequently, the thus obtained coating film is cured to form a sealing film. As a curing method, any appropriate method may be employed in accordance with the type of the sealant. When a solution of a polymer material or a suspension of inorganic microparticles is used as the sealant, the coating film may be dried at 100 to 300° C. for 60 to 300 minutes and, when a composition containing a polymer material and a cross-linking agent is used as the sealant, the coating film may be cured by thermal curing, photocuring, or the like. Further, when an organic or inorganic monomer or oligomer is used as the sealant, the curing may be performed by polymerizing the monomer or oligomer at 100 to 300° C. for 30 to 180 minutes.

When a silica film is used as the sealing film, a sealing treatment called "silicate oligomer treatment" can be performed. The silicate oligomer treatment is performed, for example, in the following manner. First, a sealant containing a silicate oligomer exemplified by an alkoxysilane compound is applied onto the bonded part. Examples of a commercially available product of the silicate oligomer include: MKC SILICATE (registered trademark) MS-51, MS-56, MS-57, and MS-56S (all of which are methyl silicate oligomers manufactured by Mitsubishi Chemical Corporation); ETHYL SILICATE 40 and ETHYL SILICATE 48 (both of which are ethyl silicate oligomers manufactured by Colcoat Co., Ltd.); and SILICATE 40 and SILICATE 45 (manufactured by Tama Chemicals Co., Ltd.); and EMS-485 (manufactured by Colcoat Co., Ltd.) which is a mixed oligomer of methyl silicate and ethyl silicate. Subsequently, the resulting coating film is heated at 150 to 280° C. for 30 to 180 minutes to carry out hydrolysis and polycondensation reaction based on a sol-gel method, whereby a silica film is obtained.

When a silicone resin is used for the sealing film, a sealant containing an oligomer of alkoxyalkylsilane may be used. Examples of such a sealant include PERMEATE HS-80, HS-90, HS-100, HS-200, HS-300, HS-330, HS-350, HS-360, and HS-820 (all of which are manufactured by D&D Corporation). A coating film obtained by applying any of these sealants is heated at 150 to 280° C. for 30 to 180 minutes to carry out hydrolysis and polycondensation reaction based on a sol-gel method, whereby a silica film is obtained.

<Separation Membrane Module>

A separation membrane module, which is another embodiment, includes a complex of a zeolite and an inorganic porous support, and a dense member. The separation membrane module may further include, for example, a container provided with an inlet and an outlet, a flange, and a pipe.

Gases and solvents can be separated by installing the separation membrane module in a high-pressure container, and applying a pressure or vacuum-evacuating the permeation side. Further, the separation membrane module may be used in a mode of performing the separation simultaneously with the reaction.

<Reactor>

By installing the separation membrane module of this embodiment into a reactor, in a production method utilizing a reaction that can accompany a reverse reaction, the natural chemical equilibrium can be constantly shifted in the direction advantageous for the production; therefore, not only the yield can be improved but also the reactor can be used for a long time with hardly any risk of breakage or the like.

<Use Conditions>

In the case of using the bonded body of the present embodiment in an organic chemical reaction process, the temperature is usually 100 to 450° C., preferably 200 to 350° C. The bonded body can also be used under a high-temperature condition of 150° C. to 500° C. Further, the pressure is usually 0.5 to 8 MPa, preferably 2 to 6 MPa. The bonded body can also be used under a high-pressure condition of 0.5 to 10 MPa.

Second Embodiment

The second embodiment of the present invention is a bonded body in which a complex of a zeolite and an inorganic porous support, and a dense member are bonded together with an inorganic glass, wherein the dense member is a metal member, and the inorganic glass has a thermal expansion coefficient of $30\times10^{-7}$/K or more and $90\times10^{-7}$/K or less and a softening point of 550° C. or lower.

<Inorganic Glass>

The inorganic glass according to the present embodiment has a thermal expansion coefficient of usually $30\times10^{-7}$/K or higher, preferably $40\times10^{-7}$/K or higher, more preferably $45\times10^{-7}$/K or higher, but usually $90\times10^{-7}$/K or lower, preferably $80\times10^{-7}$/K or lower, more preferably $75\times10^{-7}$/K or lower.

In the present embodiment, the thermal expansion coefficient of the inorganic glass is usually 60% or more, preferably 70% or more, more preferably 80% or more, but usually 200% or less, preferably 150% or less, more preferably 120% or less, of the thermal expansion coefficient of the dense member. With the thermal expansion coefficient of the inorganic glass being not higher than the above-described upper limit value, when bonding is performed at a temperature at which the inorganic glass is melted and the temperature is subsequently lowered, an internal stress is unlikely to be generated around the resulting bonded part, so that cracking of the bonded part is inhibited. Meanwhile, with the thermal expansion coefficient of the glass being not lower than the above-described lower limit value, a gap is unlikely to be generated between the complex and the dense member in the range of use temperature of the bonded body, so that a gas to be separated can be prevented from leaking through the gap to the purified gas side.

The bonded body obtained in this manner has a post-bonding air permeation amount of preferably 10 sccm or less, more preferably 8 sccm or less, most preferably 5 sccm or less, as determined by the test method described below in the section of Examples of the present specification.

Further, even when the air permeation amount is measured again after the post-bonding bonded body is heated in an autoclave to 280° C. by 1 hour with an addition of 1/16 of methanol and 1/16 of desalted water by volume with respect to the inner volume of the autoclave, maintained in this state for 48 hours, subsequently naturally cooled and then dried at 120° C. for 4 hours under normal pressure, the air permeation amount is preferably 10 sccm or less, more preferably 8 sccm or less, most preferably 5 sccm or less. This requirement is preferred to be satisfied in addition to the requirement of the thermal expansion coefficient, since this prevents a problem in a bonded part even when methanol production is carried out for a longer time.

In the industrial use of a separation module including the bonded body of the present embodiment, the separation module may be subjected to reciprocal changes between room temperature and its use temperature, and may be operated at the use temperature for a long time. Therefore, the bonded part formed by the inorganic glass is required not to have leakage of a gas to be separated even under high-temperature and high-pressure conditions, and the leakage of a gas to be separated can be inhibited by setting the thermal expansion coefficient of the inorganic glass in the above-described manner.

The inorganic glass according to the present embodiment has a softening point of 550° C. or lower, preferably 530° C. or lower, more preferably 480° C. or lower. Generally speaking, a frit of an inorganic glass can be made to flow by firing at a temperature of about 50° C. higher than its softening point. Accordingly, by controlling the softening point of the inorganic glass in the above-described range, not only the zeolite and the inorganic glass can be chemically bound at a relatively low temperature of about 600° C. or lower but also the inorganic glass is allowed to flow into pores of the complex, whereby the complex and the dense member can be mechanically and firmly bonded together. In addition, by setting the bonding temperature to be relatively low, damage to the zeolite caused by heating during bonding can be reduced. Moreover, by performing the bonding itself at a low temperature, damage to the bonded part during cooling is reduced, so that an improvement of the properties and an increase in the service life can be expected.

The inorganic glass is not particularly restricted as long as it has the above-described thermal expansion coefficient and softening point. Examples of a component contained in the inorganic glass include $SiO_2$, $Al_2O_3$, $ZnO$, $P_2O_5$, $Bi_2O_3$, $BaO$, $TiO_2$, $TeO_2$, $V_2O_5$, $B_2O_3$, $SnO$, and $PbO$. Thereamong, from the standpoint of improving the airtightness, the inorganic glass particularly preferably contains $B_2O_3$ and/or SnO. Specific examples of the inorganic glass containing $B_2O_3$ and/or SnO include an $SnO$—$P_2O_5$ glass, a $Bi_2O_3$—ZnO glass, a $Bi_2O_3$—$B_2O_3$ glass, a $Bi_2O_3$—$B_2O_3$—$SiO_2$ glass, and a $Bi_2O_3$—ZnO—$B_2O_3$ glass. Examples of a commercially available product of a glass frit of such an inorganic glass include: "FP-74", "KP312E", "FP-67", "BNL115BB", "ASF-1094", "ASF-1098", and "ASF-1109" (which are manufactured by AGC Inc.); and "BF-0606" and "BF-0901" (which are manufactured by Nippon Electric Glass Co., Ltd.).

When the inorganic glass contains SnO, the content thereof is not particularly restricted; however, it is usually 80% by mass or less, preferably 75% by mass or less, more preferably 70% by mass or less, but usually 10% by mass or higher, preferably 20% by mass or higher, more preferably 30% by mass or higher.

By controlling the SnO content in this range, the fluidity of the glass is sufficiently maintained, so that sufficient airtightness is likely to be attained. The details of the effect of adding SnO are not clear; however, SnO is known to function as a reductant, and it is presumed that SnO modifies an oxide film on the surface of the dense member and inhibits an increase in the thickness of the oxide film during a bonding treatment, consequently improving the airtightness.

Meanwhile, when the inorganic glass contains $B_2O_3$, the content thereof is usually 25% by mass or less, preferably 20% by mass or less, more preferably 18% by mass or less, still more preferably 15% by mass or less, but usually 1% by mass or higher, preferably 2% by mass or higher, more preferably 3% by mass or higher.

An addition of $B_2O_3$ improves the wettability of the inorganic glass with the dense member, so that the airtightness is likely to be improved. However, when the $B_2O_3$ content is high, the softening point tends to be increased and the choice of other component is to be limited for controlling the softening point to be 550° C. or lower; therefore, the $B_2O_3$ content is preferably selected to be in the above-described range. Further, since $B_2O_3$ is soluble in water and alcohols, the $B_2O_3$ content is preferably not higher than the above-described upper limit value when the inorganic glass has a chance of being exposed to such substances.

Examples of a method of quantifying the SnO content and the $B_2O_3$ content include an XRF (fluorescent X-ray analysis) method and an ICP (inductively-coupled plasma emission spectroscopy) method.

The form of the inorganic glass is not particularly restricted, and the inorganic glass can be used in the form of, for example, a powder glass frit, a tablet obtained by molding a glass fit by a tablet molding method or the like, a tablet obtained as a molded product by sintering a glass frit, or a glass paste obtained by uniformly dispersing a glass frit in an organic solvent or a binder. For the mass production of the bonded body, the inorganic glass is particularly preferably in the form of a tablet or a paste among the above-exemplified forms, since this leads to an improvement in the production efficiency.

Further, in the present embodiment, the inorganic glass has a lead (Pb) content of preferably 10% by mass or less, more preferably 5% by mass or less, still more preferably 3% by mass or less, yet still more preferably 2% by mass or less, particularly preferably 1% by mass or less, most preferably 0% by mass, in terms of PbO.

The lead content can also be determined by, for example, an XRF (fluorescent X-ray analysis) method or an ICP (inductively-coupled plasma emission spectroscopy) method.

The zeolite, the inorganic porous support, and the complex of the zeolite and the inorganic porous support that are used in the present embodiment are the same as in the first embodiment.

<Dense Member>

The dense member which is a member used for removing a separated gas to the outside is, for example, a pipe and has a denseness (airtightness) at a level that a gas to be treated does not leak from the member, and a metal member is used in the present invention. The metal is, for example, preferably one which has both heat resistance and corrosion resistance, and examples thereof include: SUS materials made of stainless steel; nickel-molybdenum-iron alloys (e.g., HASTELLOY (registered trademark)); inconel (nickel-chromium-iron alloy); copper; copper alloys (brass, bronze, and cupronickel); aluminum; aluminum alloys; and titanium. The metal is particularly preferably kovar (iron-cobalt-nickel alloy).

The thermal expansion coefficient of the dense member is usually $30 \times 10^{-7}$/K or more and $200 \times 10^{-7}$/K or less, and a lower limit thereof is preferably $35 \times 10^{-7}$/K or higher, more preferably $40 \times 10^{-7}$/K or higher, still more preferably $45 \times 10^{-7}$/K or higher. An upper limit is preferably $150 \times 10^{-7}$/K or lower, more preferably $120 \times 10^{-7}$/K or lower, still more preferably $85 \times 10^{-7}$/K or lower. When the thermal expansion coefficient of the dense member is in this range, a difference thereof from the thermal expansion coefficient of the inorganic glass is smaller, so that good airtightness and durability can be maintained.

It is noted here that, in the present invention, the term "thermal expansion coefficient" means a linear expansion coefficient, and indicates a rate of change of a solid in the lengthwise direction that is caused by an increase in the temperature. The thermal expansion coefficient can be measured in accordance with the method described in JIS Z2285 (Metallic Materials), JIS R1618 (Ceramics), or the like. The thermal expansion coefficient is usually measured in a range where the change in length is proportional to the change in temperature and, in the present specification, the thermal expansion coefficient is usually a value measured at 30 to 250° C.

<Bonded Body of Complex of Zeolite and Inorganic Porous Support, and Dense Member>

In the present embodiment, when the complex is a cylindrical support, both ends thereof may be bonded. For example, in the case of performing a mixed gas separation process using a zeolite membrane in which the complex is cylindrical, the outside of the cylindrical support having the zeolite membrane is filled with the mixed gas, and a pressure is applied thereto or the inside is vacuum-evacuated to execute separation. Accordingly, one end of the support may be sealed with a cap while the other end may be connected to a pipe, or both ends may be connected to a pipe.

As a method of bonding the complex having a zeolite membrane on its surface with a cap made of the dense member or with a pipe made of the dense member that has an end structure similar to that of a cap, any method may be employed as long as the complex and the cap can be bonded with the inorganic glass, and examples thereof include a method in which the inorganic glass is filled into a recess of the dense member, the complex having a zeolite membrane on its surface is placed thereon, and the dense member and the complex are subsequently fired under weighed by a weight placed on top of the complex and thereby bonded.

It is indispensable that the firing temperature for bonding the complex and the dense member using the inorganic glass be not lower than the softening point of the inorganic glass in use. Accordingly, the firing temperature is usually at least 10° C. higher than the softening point, preferably at least 30° C. higher than the softening point, more preferably at least 50° C. higher than the softening point. In order to avoid a thermal damage to the zeolite membrane, the firing temperature is usually 600° C. or lower, preferably 580° C. or lower, more preferably 560° C. or lower. Further, the firing time for the bonding is usually 5 minutes to 90 minutes, preferably 10 minutes or longer, more preferably 20 minutes or longer, but preferably 60 minutes or shorter, more preferably 40 minutes or shorter, after reaching the firing temperature.

Examples in which a complex of a zeolite and an inorganic porous support is bonded to a dense member with an inorganic glass will now be described referring to FIGS. 1 to 3.

As illustrated in FIG. 1, a complex 1 of a zeolite and an inorganic porous support can be directly bonded to a flange 11 with an inorganic glass 4. In this mode, the risks of gas leakage and the like that are associated with deterioration of the connection between members over time can be reduced. In this case, the flange 11 is a dense member made of a metal member.

Meanwhile, as illustrated in FIG. 2, the complex 1 of a zeolite and an inorganic porous support may be simply bonded to a pipe 3 with the inorganic glass 4. Such bonding is also feasible since the inorganic glass of the present embodiment has high airtightness and durability. In this case, the pipe 3 is a dense member made of a metal member.

FIG. 3 is a schematic cross-sectional view that illustrates one example in which the complex 1 of a zeolite and an inorganic porous support, and the pipe 3 are bonded with the inorganic glass 4. The complex 1 of a zeolite and an inorganic porous support is bonded to the pipe 3 with the inorganic glass 4. The pipe 3 is bonded in such a manner to cover the complex 1 of a zeolite and an inorganic porous support.

<Sealing Film>

In the present embodiment, a bonded part between the complex and the dense member is preferably covered with a sealing film. Due to the firing performed for curing the inorganic glass used for bonding, micropores such as microcracks and pinholes are formed on the surface of the bonded part in some cases. Therefore, from the standpoint of improving the airtightness, it is preferred to seal these micropores by performing a sealing treatment on the bonded part. In addition, from the standpoints of inhibiting deterioration of the bonded part and damage to the pinholes and the like, it is desirable that the bonded part be covered with a sealing film formed by the sealing treatment.

Examples of a sealant that can form the sealing film include: various inorganic materials, such as silica and alumina; organic polymers, such as silicone resins, epoxy resins, and fluorine resins, and the sealant may contain a solvent or may be solvent-free. In the present embodiment, from the standpoints of the adhesion with the inorganic glass and the gas barrier performance, it is preferred to use an inorganic sealant, particularly silica. The amount of the sealant to be adhered may be decided as appropriate in accordance with the thickness of the desired sealing film.

From the standpoint of the ease of handing of the sealant, particularly inhibition of dripping, the viscosity of the sealant is preferably 2 (mPa·s, 25° C.) or higher, more preferably 5 (mPa·s, 25° C.) or higher, still more preferably 10 (mPa·s, 25° C.) or higher. Further, from the standpoint of allowing the sealant to permeate into the holes, the viscosity is 200 (mPa·s, 25° C.) or lower, preferably 100 (mPa·s, 25° C.) or lower, more preferably 50 (mPa·s, 25° C.) or lower. By controlling the viscosity in this range, the airtightness is improved, and excellent ease of handling is attained.

As a specific method of the sealing treatment, first, the sealant is adhered to the bonded part by coating, spraying or the like to obtain a coating film. In this process, for the purpose of improving the airtightness, the pressure may be reduced on the side of the bonded part that is opposite to the side to which the sealant is adhered. This pressure reduction may be performed before, simultaneously with, or after adhering the sealant to the surface of the bonded body. By this pressure reduction, the sealant is allowed to permeate into the pores of the bonded part without any gaps, so that the pores on the surface of the bonded part can be sealed.

Subsequently, the thus obtained coating film is cured to form a sealing film. As a curing method, any appropriate method may be employed in accordance with the type of the sealant. When a solution of a polymer material or a suspension of inorganic microparticles is used as the sealant, the coating film may be dried at 100 to 300° C. for 60 to 300 minutes and, when a composition containing a polymer material and a cross-linking agent is used as the sealant, the coating film may be cured by thermal curing, photocuring, or the like. Further, when an organic or inorganic monomer or oligomer is used as the sealant, the curing may be performed by polymerizing the monomer or oligomer at 100 to 300° C. for 30 to 180 minutes.

When a silica film is used as the sealing film, a sealing treatment called "silicate oligomer treatment" can be performed. The silicate oligomer treatment is performed, for example, in the following manner. First, a sealant containing a silicate oligomer exemplified by an alkoxysilane compound is applied onto the bonded part. Examples of a commercially available product of the silicate oligomer include: MKC SILICATE (registered trademark) MS-51, MS-56, MS-57, and MS-56S (all of which are methyl silicate oligomers manufactured by Mitsubishi Chemical Corporation); ETHYL SILICATE 40 and ETHYL SILICATE 48 (both of which are ethyl silicate oligomers manufactured by Colcoat Co., Ltd.); and SILICATE 40 and SILICATE 45 (manufactured by Tama Chemicals Co., Ltd.); and EMS-485 (manufactured by Colcoat Co., Ltd.) which is a mixed oligomer of methyl silicate and ethyl silicate. Subsequently, the resulting coating film is heated at 150 to 280° C. for 30 to 180 minutes to carry out hydrolysis and polycondensation reaction based on a sol-gel method, whereby a silica film is obtained.

When a silicone resin is used for the sealing film, a sealant containing an oligomer of alkoxyalkylsilane may be used. Examples of such a sealant include PERMEATE HS-80, HS-90, HS-100, HS-200, HS-300, HS-330, HS-350, HS-360, and HS-820 (all of which are manufactured by D&D Corporation). A coating film obtained by applying any of these sealants is heated at 100° C. to 250° C. for 30 minutes to 180 minutes, whereby a silicone resin film is obtained.

<Separation Membrane Module>

A separation membrane module, which is another embodiment, includes a complex of a zeolite and an inorganic porous support, and a dense member. The separation membrane module may further include, for example, a container provided with an inlet and an outlet, a flange, and a pipe.

Gases and solvents can be separated by installing the separation membrane module in a high-pressure container, and applying a pressure or vacuum-evacuating the permeation side. Further, the separation membrane module may be used in a mode of performing the separation simultaneously with the reaction.

<Reactor>

By installing the separation membrane module of this embodiment into a reactor, in a production method utilizing a reaction that can accompany a reverse reaction, not only the yield can be improved but also the reactor can be used for a long time with hardly any risk of breakage or the like by extracting a product and/or a by-product from the reactor.

<Use Conditions>

In the case of using the bonded body of the present embodiment in a chemical reaction process, the temperature is usually 100 to 450° C., preferably 200 to 350° C. The bonded body can also be used under a high-temperature condition of 150° C. to 500° C. Further, the pressure is usually 0.5 to 8 MPa, preferably 2 to 6 MPa. The bonded body can also be used under a high-pressure condition of 0.5 to 10 MPa.

Third Embodiment

The third embodiment of the present invention is a bonded body in which a complex of a zeolite and an inorganic porous support, and a dense member are bonded together with an inorganic adhesive having a post-curing thermal expansion coefficient of $30 \times 10^{-7}$/K or more and $90 \times 10^{-7}$/K or less.

<Inorganic Adhesive>

The inorganic adhesive used in the present embodiment is characterized in that, since its main component is an inorganic substance, preferably an oxide or a nitride, it maintains a high airtightness and has excellent durability even when used under a high temperature and a high pressure while in contact with an organic solvent or an organic gas.

The inorganic adhesive used in the present embodiment is solidified by a chemical reaction and adheres, and is non-invertible to its original state even when heated. The inorganic adhesive can perform bonding usually at 200° C. or lower; therefore, it hardly damages a zeolite membrane and is thus preferred.

As the inorganic adhesive, one which contains alumina, zirconia, silica, magnesia, zircon, graphite, aluminum nitride, or a mixture thereof as a main component can be preferably used. The thermal expansion coefficient of the inorganic adhesive is generally dependent on that of the main component, and can be adjusted with an addition of other additive(s). The use of the above-described main component is preferred since it makes it easier to control the thermal expansion coefficient in the below-described preferred range.

The post-curing thermal expansion coefficient of the inorganic adhesive used in the present embodiment is usually $30 \times 10^{-7}$/K to $90 \times 10^{-7}$/K, and a lower limit thereof is preferably $35 \times 10^{-7}$/K or higher, more preferably $45 \times 10^{-7}$/K or higher, still more preferably $55 \times 10^{-7}$/K or higher. An upper limit is preferably $88 \times 10^{-7}$/K, more preferably $85 \times 10^{-7}$/K or lower, still more preferably $82 \times 10^{-7}$/K or lower.

A difference in thermal expansion coefficient between the inorganic adhesive and the dense member is preferably $50 \times 10^{-7}$/K or smaller, more preferably $40 \times 10^{-7}$/K or smaller, still more preferably $30 \times 10^{-7}$/K or smaller, yet still more preferably $15 \times 10^{-7}$/K or smaller.

A bonded body obtained by bonding the complex and the dense member by such an inorganic adhesive has an air permeation amount of preferably 100 sccm or less, more preferably 50 sccm or less, still more preferably 20 sccm or less, most preferably 10 sccm or less, as determined by the test method described below in the section of Examples of the present specification.

Further, this bonded body has an air permeation amount of preferably 100 sccm or less, more preferably 50 sccm or less, still more preferably 20 sccm or less, most preferably 10 sccm or less, even when the air permeation amount is measured again after the bonded body is heated in an autoclave to 280° C. by 1 hour with an addition of $\frac{1}{16}$ of methanol and $\frac{1}{16}$ of desalted water by volume with respect to the inner volume of the autoclave, maintained in this state for 48 hours, subsequently naturally cooled and then dried at 120° C. for 4 hours under normal pressure. This requirement is more preferred to be satisfied in addition to the requirement of the thermal expansion coefficient, since this prevents a problem in a bonded part even when methanol production is carried out for a longer time using a methanol synthesis reactor in which a separation membrane module having the bonded body is installed.

The inorganic adhesive used in the present embodiment preferably contains a metal alkoxide.

The details of the effect of adding a metal alkoxide are not clear; however, it is presumed that a metal alkoxide reacts with an oxide layer on the surface of the dense member and thereby improves the bonding strength, making cracks and pinholes less likely to be generated.

Examples of the above-described metal alkoxide include: alkali metal alkoxides, such as lithium methoxide, lithium ethoxide, sodium methoxide, sodium ethoxide, potassium methoxide, and potassium ethoxide; alkaline earth metal alkoxides, such as magnesium methoxide, magnesium ethoxide, calcium methoxide, and calcium ethoxide; alkoxides of Group 13 elements, such as boron methoxide, boron ethoxide, aluminum methoxide, aluminum ethoxide, aluminum propoxide, aluminum butoxide, gallium methoxide, and gallium ethoxide; alkoxides of Group 14 elements, such as tetramethoxysilane, tetraethoxysilane, tetrapropoxysilane, tetrabutoxysilane, methyltrimethoxysilane, methyltriethoxysilane, germanium methoxide, germanium ethoxide, tin methoxide, and tin ethoxide; alkoxides of Group 4 elements, such as titanium methoxide, titanium ethoxide, titanium propoxide, titanium butoxide, zirconium methoxide, zirconium ethoxide, zirconium propoxide, zirconium butoxide, hafnium methoxide, and hafnium ethoxide; and alkoxides of Group 5 elements, such as vanadium methoxide, vanadium ethoxide, niobium methoxide, niobium ethoxide, tantalum methoxide, and tantalum ethoxide. Examples of the metal alkoxide further include oligomers of the above-exemplified alkoxides. Among these metal alkoxides, aluminum alkoxides, such as aluminum methoxide, aluminum ethoxide, aluminum propoxide, and aluminum butoxide; silicon alkoxides, such as tetramethoxysilane, tetraethoxysilane, tetrapropoxysilane, tetrabutoxysilane, methyltrimethoxysilane, and methyltriethoxysilane; titanium alkoxides, such as titanium methoxide, titanium ethoxide, titanium propoxide, and titanium butoxide; zirconium alkoxides, such as zirconium methoxide, zirconium ethoxide, zirconium propoxide, and zirconium butoxide; and oligomers of these alkoxides are preferred, and aluminum methoxide, aluminum ethoxide, aluminum propoxide, tetramethoxysilane, tetraethoxysilane, methyltrimethoxysilane, methyltriethoxysilane, titanium ethoxide, titanium propoxide, titanium butoxide, zirconium ethoxide, zirconium propoxide, zirconium butoxide, and oligomers of these alkoxides are more preferred, since these metal alkoxides are likely to form a cross-linked structure and are readily available.

Further, the content of the metal alkoxide in the inorganic adhesive is usually 0.01 to 5% by mass, preferably 0.1% by mass or higher, more preferably 0.3% by mass or higher, but preferably 3% by mass or less, more preferably 1% by mass or less. When the content of the metal alkoxide is 0.01% by mass or higher, the physical properties are markedly improved. Meanwhile, by controlling the content of the metal alkoxide to be 5% by mass or less, not only an increase in the specific gravity is inhibited and it is advantageous in terms of cost, but also an impact-strength thereof tends to be maintained high.

As an inorganic adhesive that can be preferably used in the present embodiment, for example, "TB3732" manufactured by ThreeBond Holdings Co., Ltd. is commercially available.

The zeolite, the inorganic porous support, and the complex of the zeolite and the inorganic porous support that are used in the present embodiment are the same as in the first embodiment.

<Dense Member>

The dense member is a member which has a denseness (airtightness) at a level that a gas used for a reaction and a reacted gas do not leak from the member. The dense member is not particularly restricted as long as it has such a denseness, and a metal is typically used. Examples of the metal include: SUS materials made of stainless steel; ceramics, such as alumina and zirconia; and alloys, such as kovar.

The thermal expansion coefficient of the dense member is usually $30\times10^{-7}$/K to $200\times10^{-7}$/K, and a lower limit thereof is preferably $35\times10^{-7}$/K or higher, more preferably $40\times10^{-7}$/K or higher, still more preferably $45\times10^{-7}$/K or higher. An upper limit is preferably $150\times10^{-7}$/K or lower, more preferably $120\times10^{-7}$/K or lower, still more preferably $85\times10^{-7}$/K or lower. When the thermal expansion coefficient of the dense member is in this range, a difference thereof from the thermal expansion coefficient of the inorganic adhesive is small at, for example, $50\times10^{-7}$/K or less, so that good sealing performance (airtightness) and durability can be maintained.

It is noted here that, in the present embodiment, the term "thermal expansion coefficient" means a linear expansion coefficient, and indicates a rate of change of a solid in the lengthwise direction that is caused by an increase in the temperature. In the present specification, the thermal expansion coefficient is an average value at 30° C. to 300° C. The thermal expansion coefficient can be measured in accordance with the method described in JIS Z2285 (Metallic Materials), JIS R1618 (Ceramics), or the like.

<Bonded Body of Complex of Zeolite and Inorganic Porous Support, and Dense Member>

In the present embodiment, when the complex is a cylindrical support, both ends thereof may be bonded. For example, in the case of performing a mixed gas separation process using a zeolite membrane in which the complex is cylindrical, the outside of the cylindrical support having the zeolite membrane is filled with the mixed gas, and a pressure is applied thereto or vacuum evacuation is performed to execute separation. Accordingly, one end of the support may be sealed with a cap while the other end may be connected to a pipe, or both ends may be connected to a pipe.

As a method of bonding the complex having a zeolite membrane on its surface with a cap made of the dense member or with a pipe made of the dense member that has an end structure similar to that of a cap, any method may be employed as long as the complex and the cap can be bonded with the inorganic adhesive, and examples thereof include a method in which the inorganic adhesive is applied in advance to a side portion of the complex that comes into contact with the cap, and the cap is bonded to the complex while the cap is rotated and the bonding surface is smoothened.

After the complex and the dense member are bonded with the inorganic adhesive, as required, the resultant is left to stand at room temperature for usually 1 to 24 hours and subsequently fired to complete the bonding. In the present embodiment, the term "room temperature" means 15 to 30° C.

The firing temperature for the bonding is usually 80 to 200° C., preferably 90° C. or higher, more preferably 100° C. or higher, but preferably 180° C. or lower, more preferably 150° C. or lower. The firing time for the bonding is usually 10 to 300 minutes, preferably 30 minutes or longer, more preferably 60 minutes or longer, but preferably 180 minutes or shorter, more preferably 120 minutes or shorter.

Examples in which a complex of a zeolite and an inorganic porous support is bonded to a dense member with an inorganic adhesive will now be described referring to FIGS. 1 to 3.

As illustrated in FIG. 1, a complex 1 of a zeolite and an inorganic porous support can be directly bonded to a flange 11 with an inorganic adhesive 4. In this mode, the risks of gas leakage and the like that are associated with deterioration of the connection between members over time can be reduced. In this case, the flange 2 is a dense member.

Meanwhile, as illustrated in FIG. 2, the complex 1 of a zeolite and an inorganic porous support may be simply bonded to a pipe 3 with the inorganic adhesive 4. Such bonding is also feasible since the inorganic adhesive of the present embodiment has high airtightness and durability. In this case, the pipe 3 is a dense member.

FIG. 3 is a schematic cross-sectional view that illustrates one example in which the complex 1 of a zeolite and an inorganic porous support, and the pipe 3 are bonded with the inorganic adhesive 4. The complex 1 of a zeolite and an inorganic porous support is bonded to the pipe 3 with the inorganic adhesive 4. The pipe 3 is bonded in such a manner to cover the complex 1 of a zeolite and an inorganic porous support.

It is noted here that the term "bonded body" used in the present invention refers to a component in which a complex of a zeolite and an inorganic porous support is bonded to a dense member and which is detachable for replacement when the performance of the complex is deteriorated. In cases where the bonded body does not have such a detachable mechanism, such as a case where the bonded body is integrated into a methanol synthesis reactor or the like, the bonded body also includes the dense member existing inside the reactor.

<Sealing Film>

In the present embodiment, a bonded part between the complex and the dense member is preferably covered with a sealing film. Due to the firing performed for curing the inorganic adhesive used for bonding, micropores such as microcracks and pinholes are formed on the surface of the bonded part in some cases. Therefore, from the standpoint of improving the sealing performance (airtightness), it is preferred to seal these micropores by performing a sealing treatment on the bonded part. In addition, from the standpoints of inhibiting deterioration of the bonded part and damage to the pinholes and the like, it is desirable that the bonded part be covered with a sealing film formed by the sealing treatment.

Examples of a sealant that can form the sealing film include: various inorganic materials, such as silica and alumina; organic polymers, such as silicone resins, epoxy resins, and fluorine resins, and the sealant may contain a solvent or may be solvent-free. In the present embodiment, from the standpoints of the adhesion with the inorganic adhesive and the gas barrier performance, it is preferred to use an inorganic sealant, particularly silica. Further, from the standpoint of forming a dense film, it is also suitable to use a silicone resin. The amount of the sealant to be adhered may be decided as appropriate in accordance with the thickness of the desired sealing film. From the standpoint of the ease of handing of the sealant, particularly inhibition of dripping, the viscosity of the sealant is preferably 2 (mPa·s, 25° C.) or higher, more preferably 5 (mPa·s, 25° C.) or higher, still more preferably 10 (mPa·s, 25° C.) or higher. Further, from the standpoint of allowing the sealant to permeate into the holes, the viscosity is 200 (mPa·s, 25° C.) or lower, preferably 100 (mPa·s, 25° C.) or lower, more preferably 50 (mPa·s, 25° C.) or lower. By controlling the viscosity in this range, the sealing performance is improved, and excellent ease of handling is attained.

As a specific method of the sealing treatment, first, the sealant is adhered to the bonded part by coating, spraying or the like to obtain a coating film. In this process, for the purpose of improving the sealing performance (airtightness), the pressure may be reduced on the side of the bonded part that is opposite to the side to which the sealant is adhered. This pressure reduction may be performed before, simultaneously with, or after adhering the sealant to the surface of the bonded body. By this pressure reduction, the sealant is allowed to permeate into the pores of the bonded part without any gaps, so that the pores on the surface of the bonded part can be sealed.

Subsequently, the thus obtained coating film is cured to form a sealing film. As a curing method, any appropriate method may be employed in accordance with the type of the sealant. When a solution of a polymer material or a suspension of inorganic microparticles is used as the sealant, the coating film may be dried at 100 to 300° C. for 60 to 300 minutes and, when a composition containing a polymer material and a cross-linking agent is used as the sealant, the coating film may be cured by thermal curing, photocuring, or the like. Further, when an organic or inorganic monomer or oligomer is used as the sealant, the curing may be performed by polymerizing the monomer or oligomer at 100 to 300° C. for 30 to 180 minutes.

When a silica film is used as the sealing film, a sealing treatment called "silicate oligomer treatment" can be performed. The silicate oligomer treatment is performed, for example, in the following manner. First, a sealant containing a silicate oligomer exemplified by an alkoxysilane compound is applied onto the bonded part. Examples of a commercially available product of the silicate oligomer include: MKC SILICATE (registered trademark) MS-51, MS-56, MS-57, and MS-56S (all of which are methyl silicate oligomers manufactured by Mitsubishi Chemical Corporation); ETHYL SILICATE 40 and ETHYL SILICATE 48 (both of which are ethyl silicate oligomers manufactured by Colcoat Co., Ltd.); and SILICATE 40 and SILICATE 45 (manufactured by Tama Chemicals Co., Ltd.); and EMS-485 (manufactured by Colcoat Co., Ltd.) which is a mixed oligomer of methyl silicate and ethyl silicate. Subsequently, the resulting coating film is heated at 150 to 280° C. for 30 to 180 minutes to carry out hydrolysis and polycondensation reaction based on a sol-gel method, whereby a silica film is obtained.

When a silicone resin is used for the sealing film, a sealant containing an oligomer of alkoxyalkylsilane may be used. Examples of such a sealant include PERMEATE HS-80, HS-90, HS-100, HS-200, HS-300, HS-330, HS-350, HS-360, and HS-820 (all of which are manufactured by D&D Corporation). A coating film obtained by applying any of these sealants is heated at 100° C. to 250° C. for 30 minutes to 180 minutes, whereby a silicone resin film is obtained.

<Separation Membrane Module>

A separation membrane module, which is another embodiment, includes a complex of a zeolite and an inorganic porous support, and a dense member. The separation membrane module may further include, for example, a container provided with an inlet and an outlet, a flange, and a pipe.

Gases and solvents can be separated by installing the separation membrane module in a high-pressure container, and applying a pressure or vacuum-evacuating the permeation side.

Further, the separation membrane module may be used in a mode of performing the separation simultaneously with the reaction.

<Reactor>

By installing the separation membrane module of this embodiment into a reactor, in a production method utilizing a reaction that can accompany a reverse reaction, the natural chemical equilibrium can be constantly shifted in the direction advantageous for the production; therefore, not only the yield can be improved but also the reactor can be used for a long time with hardly any risk of breakage or the like.

<Use Conditions>

In a method of using the bonded body of the present embodiment in a reaction process, the temperature is usually 100 to 450° C., preferably 200 to 350° C. The bonded body can also be used under a high-temperature condition of 100° C. to 500° C. Further, the pressure is usually 0.5 to 8 MPa, preferably 2 to 6 MPa. The bonded body can also be used under a high-pressure condition of 0.5 to 10 MPa.

Fourth Embodiment

The fourth embodiment of the present invention is a methanol production method of obtaining methanol by allowing a raw material gas, which contains at least hydrogen and carbon monoxide and/or carbon dioxide, to react in the presence of a catalyst in a reactor.

A content ratio of hydrogen ($H_2$) and carbon monoxide and/or carbon dioxide (hereinafter, may be collectively referred to as "CON") in the raw material gas is not particularly restricted; however, a ratio $H_2:CO_x$ is usually 4:6 to 9:1, preferably 5:5 to 8:2, in terms of volume ratio.

The raw material gas may also contain a gas other than $H_2$ and $CO_x$. Examples of the gas other than $H_2$ and $CO_x$ include $CH_4$, $C_2H_4$, $C_2H_6$, $C_3H_6$, $C_3H_8$, $C_4H_8$, $C_4H_{10}$ and $H_2O$, and the content of the gas other than $H_2$ and $CO_x$ is usually 50% by volume or less.

The catalyst used for the production of methanol from the raw material gas may be any known catalyst, and examples thereof include copper-based catalysts (copper-zinc-based catalysts and copper-chromium-based catalysts), zinc-based catalysts, chromium-based catalysts, and aluminum-based catalysts.

In the present embodiment, a methanol-selective permeable membrane, which is bonded to a dense member with a bonding material that contains an inorganic oxide as a main component and that has a linear expansion coefficient of $30 \times 10^{-7}$/K or more and $90 \times 10^{-7}$/K or less, is installed in the reactor used for obtaining methanol. This feature will now be described referring to the drawings. It is noted here that, in the present specification, the linear expansion coefficient of a bonding material is the linear expansion coefficient of the bonding material determined after bonding (after firing), and indicates a rate of change of a solid in the lengthwise direction that is caused by an increase in the temperature. The linear expansion coefficient can be measured in accordance with the method described in JIS Z2285 (Metallic Materials), JIS R1618 (Ceramics), or the like. In the present specification, the linear expansion coefficient is an average value at 30° C. to 300° C.

Figure 4:
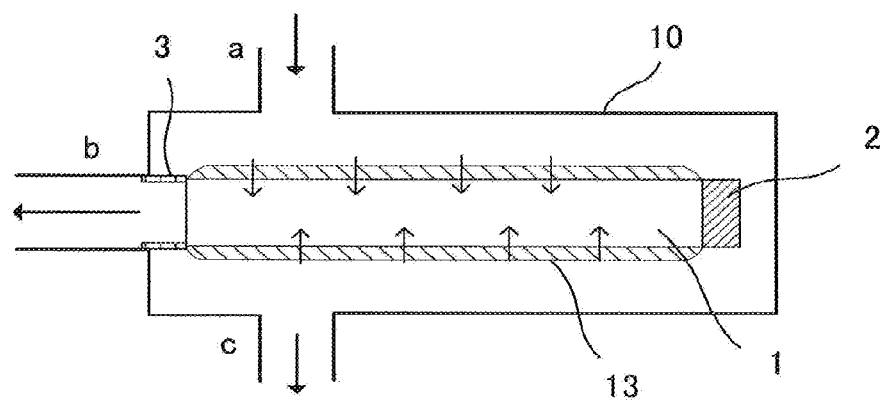
FIG. 4 is a schematic cross-sectional view that illustrates one mode of a reactor.

FIG. 4 is a schematic cross-sectional view that illustrates one mode of a reactor in which the present invention is carried out.

A reactor 10 includes: a raw material feed inlet a; a permeated gas outlet b; and a non-permeated gas outlet c. Since a methanol synthesis reaction is carried out at a high temperature and a high pressure, the reactor 10 is made of a material that can withstand such an environment. The inlet a, the outlet b, and the outlet c each exist singly in FIG. 4; however, they may each exist plurally.

In the reactor 10, a zeolite membrane complex 1, which is a methanol-selective permeable membrane, is installed. The methanol-selective permeable membrane is not particularly restricted in terms of its type as long as it is capable of selectively allowing methanol to permeate therethrough; however, a zeolite membrane is typically used. The zeolite membrane complex will be described below in detail.

The zeolite membrane complex 1 is a complex obtained by forming a zeolite membrane on a porous support. The shape of the porous support is not restricted to be tubular, and the porous support may have a columnar shape, a hollow columnar shape, or a hollow honeycomb shape. One end of the zeolite membrane complex 1 is hermetically sealed with a cap 2, and the other end is connected to a pipe 3. The pipe 3 and the zeolite complex 1, and the cap 2 and the zeolite complex 1 are connected and bonded to each other with the below-described bonding material. A method for connecting the zeolite membrane complex is not restricted to the above-described method and, for example, both ends of the zeolite membrane complex may each be connected to a pipe such that a gas can be circulated inside.

A catalyst 13 is arranged around the tubular zeolite membrane complex 1. A raw material gas fed via the feed inlet a comes into contact with the catalyst 13, and the methanol generation is thereby facilitated. The thus generated methanol permeates through the zeolite membrane of the zeolite membrane complex 1, whereby methanol having a higher purity can be obtained. Further, as a result of the selective permeation of methanol through the zeolite complex 1, the methanol concentration in the gas coming into contact with the catalyst 13 is reduced, and the methanol generation is facilitated.

The other end of the pipe 3 is connected to the permeated gas outlet b of the reactor, and methanol permeating through the zeolite membrane of the zeolite membrane complex 1 is transferred therethrough to the permeated gas outlet b. It is noted here that the zeolite membrane complex 1 may be directly connected to the permeated gas outlet b of the reactor without the pipe 3.

In the present embodiment, the methanol-selective permeable membrane is bonded to a dense member with a bonding material which contains an inorganic oxide as a main component and has a linear expansion coefficient of $30 \times 10^{-7}$/K or more and $90 \times 10^{-7}$/K or less.

As the inorganic oxide, one which can be used as an inorganic adhesive may be selected as appropriate.

The term "inorganic adhesive" used herein refers to a substance that is solidified by a chemical reaction and adheres, and is invertible to its original state even when heated. The inorganic adhesive can perform bonding usually at 200° C. or lower; therefore, it hardly damages a zeolite membrane and is thus preferred. The inorganic oxide may be an inorganic glass as well. Examples of the inorganic oxide include alumina, titania, zirconia, silica, and magnesia. Examples of the inorganic glass include those which contain $SiO_2$, $Al_2O_3$, ZnO, $P_2O_5$, $Bi_2O_3$, BaO, $TiO_2$, $TeO_2$, $V_2O_5$, $B_2O_3$, SnO or the like as a component, and the inorganic glass is preferably a lead-free inorganic glass.

The term "main component" used herein means a component having the highest content (largest mass) among all components constituting the bonding material, and the content of the main component is usually 50% by mass or higher, and may be 70% by mass or higher, 80% by mass or higher, or 90% by mass or higher, in all components. In a more preferred condition, the softening point is 550° C. or lower. Bonding by such a glass is carried out by heating the glass to a temperature of about 50° C. higher than the softening point and subsequently cooling the glass. Therefore, a glass having a softening point of higher than 550° C. is not preferred since it damages zeolite. Such a phenomenon presents a risk that the zeolite surface state is modified and the methanol selectivity is deteriorated when the zeolite-containing separation membrane used in the present invention is exposed to a temperature of 600° C. or higher since the zeolite-containing separation membrane is a methanol-selective permeable membrane through which methanol having a large molecular size easily permeates but smaller raw materials such as carbon dioxide hardly permeate.

The bonding material has a linear expansion coefficient of $30 \times 10^{-7}$/K or more and $90 \times 10^{-7}$/K or less and is thus capable of improving the adhesion between the methanol-selective permeable membrane and the dense member and providing good sealing performance and durability. The linear expansion coefficient of the bonding material is preferably $40 \times 10^{-7}$/K or higher, but preferably $80 \times 10^{-7}$/K or lower.

The linear expansion coefficient of the bonding material is generally dependent on that of the main component, and can be adjusted by mixing the main component with other additive(s). In order to control the linear expansion coefficient to be $30 \times 10^{-7}$/K to $90 \times 10^{-7}$/K, it is preferred to use alumina, zirconia, silica, graphite, $P_2O_5$, $Bi_2O_3$, SnO, or the like as the main component.

As the bonding material, a commercially available product may be used as well, and examples thereof include: "TB3732" manufactured by ThreeBond Holdings Co., Ltd.; "ARON CERAMIC D" and "ARON CERAMIC E", which are manufactured by Toagosei Co., Ltd.; "FP-74", "KP312E", "FP-67", "BNL115BB", "ASF-1094", "ASF-1098" and "ASF-1109", which are manufactured by AGC Inc.; and "CERAMABOND 552" manufactured by Aremco Products Inc.

The dense member bonded to the methanol-selective permeable membrane with the bonding material is a member which has a denseness (airtightness) at a level that a gas used for a reaction and a reacted gas do not leak from the member, and examples of the dense member include a cap that seals an end of a tubular member, and a pipe connected with an end of a tubular member. The dense member is not particularly restricted as long as it has such a denseness, and a metal is typically used. Examples of the metal include: SUS materials made of stainless steel; ceramics, such as alumina and zirconia; and alloys, such as kovar.

In the present embodiment, the dense member has a linear expansion coefficient of preferably $30\times10^{-7}$/K or more and $200\times10^{-7}$/K or less. When the linear expansion coefficient of the dense member is in this range, a difference thereof from the linear expansion coefficient of the bonding material is small, so that good sealing performance and durability can be maintained.

The difference in linear expansion coefficient between the bonding material and the dense member is preferably $50\times10^{-7}$/K or smaller, more preferably $40\times10^{-7}$/K or smaller, still more preferably $30\times10^{-7}$/K or smaller. When the difference in linear expansion coefficient between the bonding material and the dense member is small in this manner, bonding defects caused by shrinkage of a material during sintering of the bonding material can be inhibited.

Examples in which, as a methanol-permeable membrane, a zeolite membrane complex and a dense member are bonded together with a bonding material, will now be described referring to FIGS. 5 to 7.

Figure 5:
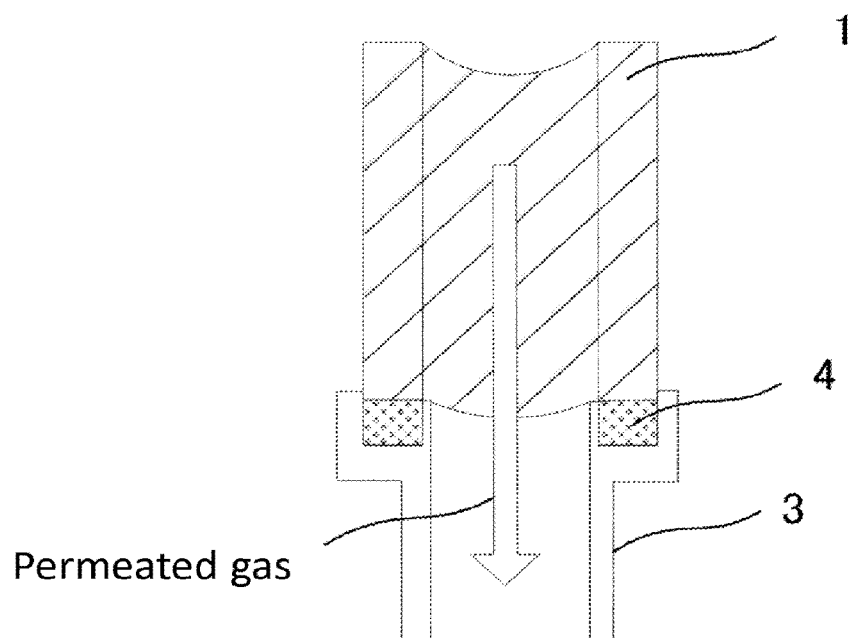
FIG. 5 is a schematic cross-sectional view that illustrates a mode in which a zeolite membrane and the flange of a pipe are bonded using a bonding material.

FIG. 5 is a schematic cross-sectional view that illustrates one example in which a zeolite membrane complex and a dense member bonded together with a bonding material. A zeolite membrane complex 1 is bonded to a pipe 3 with a bonding material 4. The pipe 3 is bonded in such a manner to cover the zeolite membrane complex 1.

Figure 6:
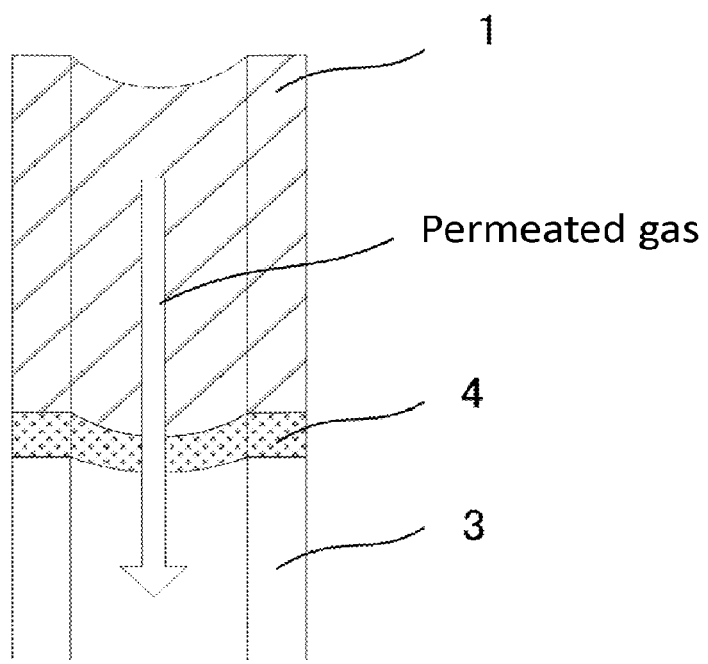
FIG. 6 is a schematic cross-sectional view that illustrates a mode in which a zeolite membrane and a pipe are bonded using a bonding material.

Meanwhile, as illustrated in FIG. 6, the zeolite membrane complex 1 and the pipe 3 may be simply bonded with the bonding material. Such bonding is also feasible since the bonding material of the present embodiment has high sealing performance and durability.

Figure 7:
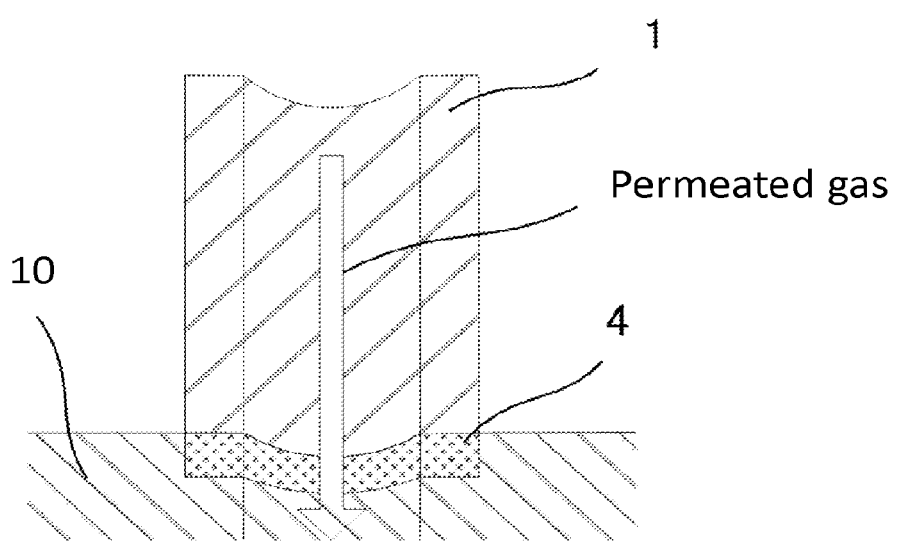
FIG. 7 is a schematic cross-sectional view that illustrates a mode in which a zeolite membrane and a reactor are bonded using a bonding material.

Further, as illustrated in FIG. 7, the zeolite membrane complex 1 and a reactor 10 may be directly bonded with the bonding material 4. In this mode, because of the absence of a pipe, not only the cost of a production apparatus can be reduced, but also the risks of gas leakage and the like that are associated with deterioration of the connection between members over time can be reduced.

The methanol-selective permeable membrane of the present embodiment is typically a zeolite membrane; however, it is not particularly restricted as long as it can selectively allow methanol to permeate therethrough and, for example, various porous membranes and MOFs (Metal Organic Frameworks) can be used as well.

In one mode, the zeolite membrane is formed on a porous support member made of alumina or the like, and used as a zeolite membrane complex.

A zeolite mainly constituting the zeolite membrane is preferably one which contains a zeolite having a pore structure of 6- to 12-membered oxygen ring.

The value n of the above-described zeolite having an n-membered oxygen ring indicates the number of oxygen atoms in a pore having the largest number of oxygen atoms among the pores formed by oxygen constituting a zeolite skeleton and T elements (elements other than oxygen constituting the skeleton). For example, when pores of 12-membered oxygen rings and pores of 8-membered rings exist as in the case of an MOR-type zeolite, the zeolite is considered to have a 12-membered oxygen ring.

Examples of the zeolite having a pore structure of 6- to 12-membered oxygen ring include, in terms of the codes defined by the International Zeolite Association (IZA): AEI, AEL, AFI, AFC, ANA, ATO, BEA, BRE, CAS, CDO, CHA, CON, DDR, DOH, EAB, EPI, ERI, ESV, EUO, FAR, FAU, FER, FRA, HEU, GIS, GIU, GME, GOO, ITE, KFI, LEV, LIO, LOS, LTA, LTL, LTN, MAR, MEP, MER, MEL, MFI, MON, MOR, MSO, MTF, MTN, MTW, MWW, NON, NES, OFF, PAU, PHI, RHO, RTE, RTH, RUT, SGT, OD, STI, STT, TOL, TON, TSC, UFI, VNI, WEI, and YUG. The zeolite is preferably any one selected from these zeolites.

Further, a zeolite particularly suitably used in the present invention is more preferably able to selectively adsorb a target substance by the zeolite for the purpose of, for example, allowing large-sized molecules to permeate therethrough or separating molecules of comparable sizes from one another, rather than one as a simple molecular sieve, namely for the purpose of allowing molecules to permeate therethrough, simply based on molecular size differences. In other words, a zeolite that separates molecules based on selective adsorption thereof to the zeolite surface is more preferred. The selective adsorption capacity of such zeolite is decreased when the temperature is increased; therefore, the effects of the present invention are more prominently exerted.

A zeolite is poor in flexibility; therefore, when it is made into a membrane, the membrane is produced in the form of being supported on a substrate. A support is a porous such that gas molecules can penetrate thereinto and, for example, the support has a large number of three-dimensionally connected fine small holes.

A material constituting the support is preferably chemically stable enough not to react with an untreated gas, and preferably has excellent mechanical strength. Specifically, various oxide ceramics, such as alumina, silica, silica-alumina, mullite, cordierite and zirconia, as well as silicon carbide, carbon, and glass can be used.

The shape of the support varies depending on the intended use of the zeolite membrane; however, particularly, a zeolite membrane on a cylindrical support is strong against a pressure from the outside, and is thus suitable for the simple use in a batch process, a circulation process (recycle process), and the like.

In the present embodiment, a zeolite membrane complex in which a zeolite membrane is formed on a support can be used. The zeolite membrane complex is obtained by, for example, preparing a cylindrical support and, first, supporting zeolite microcrystals inside its pores. As a supporting method, for example, a dipping method, a rubbing method, a suction method, or an impregnation method can be employed. The microcrystals, which play a role as nuclei for the growth of crystals constituting the zeolite membrane, are also referred to as "seed crystals". For the growth of zeolite, hydrothermal synthesis can be employed in the same manner as in the zeolite synthesis.

The thickness of the zeolite membrane in the zeolite membrane complex is not particularly restricted; however, it is usually 0.1 μm or greater, preferably 0.5 μm or greater, but usually 50 μm or less, preferably 20 μm or less. By controlling the thickness of the zeolite membrane to be a certain value or greater, a sufficient denseness is obtained, and the selectivity of the membrane is maintained high. Further, by controlling the thickness of the zeolite membrane to be a certain value or less, a sufficient gas permeation amount is obtained.

In the present embodiment, methanol is obtained by allowing a raw material gas, which contains at least hydrogen and carbon monoxide and/or carbon dioxide, to react in the presence of a catalyst in a reactor. The reaction conditions are not particularly restricted; however, the reaction temperature is preferably 200° C. to 300° C. The "reaction temperature" means the temperature of the inside of the reactor. By controlling the reaction temperature to be 200° C. or higher, the reaction rate is increased, and the productivity is thus improved. By controlling the reaction temperature to be 300° C. or lower, the chemical equilibrium of the reaction is made advantageous for obtaining methanol; therefore, a high conversion rate can be attained even when the membrane performance is somewhat deteriorated. In addition, the acceptable range of the heat resistance required for a bonding material is widened.

Methanol generated by the reaction permeates through a methanol-selective permeable membrane provided in the reactor, and is recovered from a permeated gas outlet of the reactor.

The pressure in the reactor when allowing the generated methanol to permeate through the methanol-selective permeable membrane, namely the pressure (gauge pressure) on the gas supply side of the methanol-selective permeable membrane in the reactor, is preferably 1 MPaG or higher, more preferably 2 MPaG or higher, but preferably 8 MPaG or lower, more preferably 5 MPaG or lower. By controlling the pressure in an appropriate range, the equilibrium constrain of the reaction is reduced and the reaction rate is increased, so that a higher productivity is likely to be achieved. In addition, an increase in the production cost of the reactor and an increase in the cost for increasing the pressure of the raw material gas, due to an excessively high pressure, can be inhibited.

Further, in the reactor, the methanol partial pressure (absolute pressure) on the gas supply side of the methanol-selective permeable membrane is preferably 0.1 MPaA or higher, more preferably 0.2 MPaA or higher, but preferably 6 MPaA or lower, more preferably 5 MPaA or lower. By controlling the methanol partial pressure in this range, methanol permeating through the membrane is obtained in a sufficient amount, and the effect of the membrane is exerted favorably. In addition, with the methanol partial pressure being in this range, the durability and the sealing performance that are required for a bonded part are not excessively high more than necessary, and bonding can thus be carried out easily and in a large amount.

The gauge pressure in the reactor can be measured using a pressure gage provided in the reactor. The absolute pressure of methanol in the reactor varies from the upstream to the downstream of the reactor; however, in the present embodiment, a value calculated from the results of analyzing the composition of the reactor outlet gas by gas chromatography and the gauge pressure is defined as the absolute pressure of methanol in the reactor.

Fifth Embodiment

The fifth embodiment of the present invention is an alcohol production apparatus for synthesizing an alcohol by allowing raw materials, which contain at least hydrogen and carbon monoxide and/or carbon dioxide, to react in the presence of a catalyst,
wherein the production apparatus includes: a reactor equipped with a zeolite-containing alcohol-selective permeable membrane; heat recovery means for recovering at least some of reaction heat from the reactor; and heat supply means for supplying the heat recovered by the heat recovery means.

Another mode of the fifth embodiment of the present invention is an alcohol production method, including a synthesis step of synthesizing an alcohol by allowing raw materials, which contain at least hydrogen and carbon monoxide and/or carbon dioxide, to react in the presence of a catalyst,
wherein the alcohol production method further includes:
a separation-recovery step of separating and recovering the thus obtained alcohol in a reactor using a zeolite-containing alcohol-selective permeable membrane; and
a heat recovery step of recovering at least some of reaction heat generated in the synthesis step from the reactor, and
the separation-recovery step and the heat recovery step are carried out concurrently.

Representative modes of carrying out the fifth embodiment will now be described concretely; however, within the gist of the present invention, the present invention is not restricted to the below-described modes, and can be carried out with various modifications.

One embodiment of the present invention is an alcohol production apparatus for synthesizing an alcohol by allowing raw materials, which contain at least hydrogen and carbon monoxide and/or carbon dioxide, to react in the presence of a catalyst, and this production apparatus includes: a reactor equipped with a zeolite-containing alcohol-selective permeable membrane; heat recovery means for recovering at least some of reaction heat from the reactor; and heat supply means for supplying the heat recovered by the heat recovery means.

A content ratio of hydrogen ($H_2$) and carbon monoxide and/or carbon dioxide (hereinafter, may be collectively referred to as "$CO_x$") in a raw material gas is not particularly restricted; however, a ratio $H_2:CO_x$ is usually 4:6 to 9:1, preferably 5:5 to 8:2, in terms of volume ratio.

The raw material gas may also contain a gas other than $H_2$ and CON. Examples of the gas other than $H_2$ and $CO_x$ include $CH_4$, $C_2H_4$, $C_2H_6$, $C_3H_6$, $C_{3118}$, $C_4H_8$, $C_4H_{10}$ and $H_2O$, and the content of the gas other than $H_2$ and $CO_x$ is usually 50% by volume or less.

The raw material that has been preheated is introduced to the reactor, and an alcohol is synthesized therefrom by a catalyst arranged in the reactor. The alcohol may be a lower alcohol having 1 to 4 carbon atoms, preferably an alcohol having 1 to 3 carbon atoms, most preferably methanol.

The catalyst used for the production of an alcohol from the raw material gas may be any known catalyst, and examples thereof include copper-based catalysts (copper-zinc-based catalysts and copper-chromium-based catalysts), zinc-based catalysts, chromium-based catalysts, and aluminum-based catalysts.

The synthesis of an alcohol by a catalyst is an equilibrium reaction. In this equilibrium reaction, mainly the following three reactions take place, as a result of which an alcohol (methanol) is generated.

$$3H_2 + CO_2 \rightarrow CH_3OH + H_2O \qquad \text{Formula 1}$$

$$2H_2 + CO \rightarrow CH_3OH \qquad \text{Formula 2}$$

$$CO_2 + H_2 \rightarrow CO + H_2O \qquad \text{Formula 3}$$

During the reactions synthesizing an alcohol, the alcohol (methanol in the above-described Formulae) is recovered using a zeolite-containing alcohol-selective permeable membrane, whereby the yield of the alcohol can be improved.

Further, in the present invention, means for recovering the reaction heat (heat recovery means) is arranged in the reactor that carries out the reactions. By this, an excessive temperature increase in the reactor is inhibited, and the reaction is prevented from shifting in the direction of facilitating alcoholysis. For this purpose, it is preferred to control the temperature in the reactor. The temperature in the reactor is usually 200° C. or higher, preferably 210° C. or higher, more preferably 220° C. or higher, but usually 300° C. or lower, preferably 290° C. or lower, more preferably 270° C. or lower. The temperature in the reactor may be any combination of these upper limit values and lower limit values. This temperature is the temperature of the gas in the reactor, and can be determined by measuring the temperature of a mixture of unreacted raw material gas and alcohol that is released from the reactor.

The means for recovering the reaction heat is not particularly restricted and, for example, a heat exchanger or a steam generator can be used.

The alcohol, which has permeated through the alcohol-selective permeable membrane and has been thereby separated, inevitably contains the raw materials; therefore, the temperature of the alcohol permeated through the alcohol-selective permeable membrane is lowered to liquefy the alcohol, and this alcohol is separated from hydrogen, carbon dioxide and/or carbon monoxide that are unreacted raw materials. Further, a line in which the gas does not pass through the alcohol-selective permeable membrane may be arranged in the reactor and, since the unreacted raw materials and the alcohol are released into this line as well, this alcohol is liquefied by lowering the temperature in the same manner as in the case of the gas permeated through the alcohol-selective permeable membrane, whereby the alcohol is separated from hydrogen, carbon dioxide and/or carbon monoxide that are unreacted raw materials. This process is gas-liquid separation, and the temperature of the gas-liquid separation varies depending on the alcohol to be obtained; however, in the case of methanol, the temperature is usually 60° C. or lower, preferably 50° C. or lower, more preferably 40° C. or lower.

The unreacted raw materials recovered in this manner are mixed with fresh raw materials, preheated again, and then introduced into the reactor. The means for preheating the raw materials before the introduction into the reactor is not particularly restricted; however, by preheating the raw materials using the thermal energy obtained by the heat recovery means for recovering the reaction heat, the thermal energy can be efficiently utilized.

In addition to the preheating of the raw materials, examples of the use of the recovered thermal energy include heating for purification of a product, heating for adjusting the product to have a temperature suitable for a subsequent process, generation of steam to be used in the process, and power generation using the generated steam.

In the present invention, means for utilizing the energy recovered by the heat recovery means in a process in the above-exemplified manner are collectively referred to as "heat supply means".

(Description of Apparatus)

One example of the apparatus of the present embodiment will now be described referring to FIG. 9.

Figure 9:
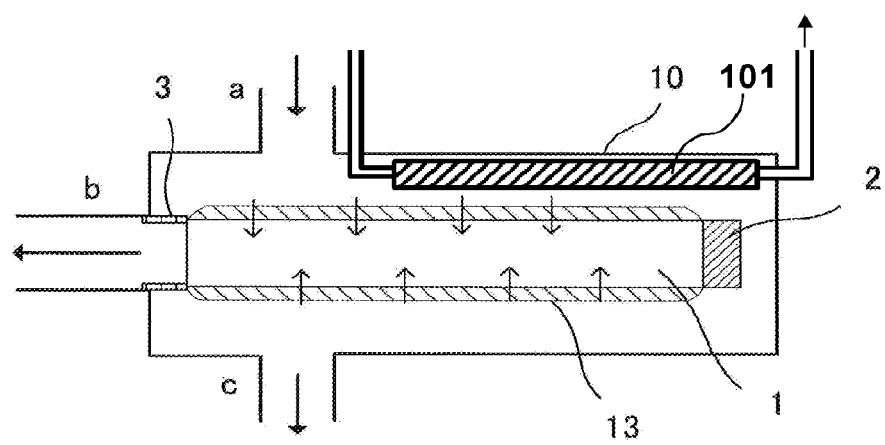
FIG. 9 is a schematic cross-sectional view that illustrates one mode of a reactor having a heat exchanger.

FIG. 9 is a schematic cross-sectional view that illustrates one example of a reactor used in the present embodiment.

A reactor 10 includes: a raw material feed inlet a; a permeated gas outlet b; and a non-permeated gas outlet c. Since an alcohol synthesis reaction is carried out at a high temperature and a high pressure, the reactor 10 is made of a material that can withstand such an environment. The inlet a, the outlet b, and the outlet c each exist singly in FIG. 9; however, they may each exist plurally.

In the reactor 10, a zeolite membrane complex 1, which is an alcohol-selective permeable membrane, is installed. The alcohol-selective permeable membrane is not particularly restricted in terms of its type as long as it is capable of selectively allowing an alcohol to permeate therethrough; however, a zeolite membrane is typically used. The zeolite membrane complex will be described below in detail.

The zeolite membrane complex 1 is a complex obtained by forming a zeolite membrane on a porous support. The shape of the porous support is not restricted to be tubular, and the porous support may have a columnar shape, a hollow columnar shape, or a hollow honeycomb shape. One end of the zeolite membrane complex 1 is hermetically sealed with a cap 2, and the other end is connected to a pipe 3. The pipe 3 and the zeolite complex 1, and the cap 2 and the zeolite complex 1 are connected and bonded to each other with the below-described bonding material. A method for connecting the zeolite membrane complex is not restricted to the above-described method and, for example, both ends of the zeolite membrane complex may each be connected to a pipe such that a gas can be circulated inside.

A catalyst 13 is arranged around the tubular zeolite membrane complex 1. A raw material gas fed via the feed inlet a comes into contact with the catalyst 13, and the alcohol generation is thereby facilitated. The thus generated alcohol permeates through the zeolite membrane of the zeolite membrane complex 1, whereby alcohol having a higher purity can be obtained. Further, as a result of the selective permeation of alcohol through the zeolite complex 1, the alcohol concentration in the gas coming into contact with the catalyst 13 is reduced, and the alcohol generation is facilitated.

The other end of the pipe 3 is connected to the permeated gas outlet b of the reactor, and the alcohol permeating through the zeolite membrane of the zeolite membrane complex 1 is transferred therethrough to the permeated gas outlet b. It is noted here that the zeolite membrane complex 1 may be directly connected to the permeated gas outlet b of the reactor without the pipe 3.

In the present embodiment, a heat exchanger 101, which is heat recovery means for recovering at least some of the reaction heat from the reactor 10, is arranged. As this heat recovery means, a heat exchanger is typically used. The heat recovery means may be arranged plurally. The heat recovery means may be arranged inside the reactor 10, or adjacent to the reactor 10.

The alcohol-selective permeable membrane is preferably bonded to a dense member with a bonding material which contains an inorganic oxide as a main component and has a linear expansion coefficient of $30 \times 10^{-7}$/K or more and $90 \times 10^{-7}$/K or less.

As the inorganic oxide, one which can be used as an inorganic adhesive may be selected as appropriate. The inorganic oxide may be an inorganic glass as well. Examples of the inorganic oxide include alumina, titania, zirconia, silica, and magnesia. Examples of the inorganic glass include those which contain $SiO_2$, $Al_2O_3$, $ZnO$, $P_2O_5$, $Bi_2O_3$, $BaO$, $T_1O_2$, $TeO_2$, $V_2O_5$, $B_2O_3$, $SnO$ or the like as a component, and the inorganic glass is preferably a lead-free glass.

The term "main component" used herein means a component having the highest content (largest mass) among all components constituting the bonding material, and the content of the main component is usually 50% by mass or higher, and may be 70% by mass or higher, 80% by mass or higher, or 90% by mass or higher, in all components.

The bonding material has a linear expansion coefficient of usually $30\times10^{-7}$/K or higher, preferably $40\times10^{-7}$/K or higher, but usually $90\times10^{-7}$/K or lower, preferably $80\times10^{-7}$/K or lower. When the linear expansion coefficient of the bonding material is in this range, the adhesion between the alcohol-selective permeable membrane and the dense member is improved, so that good sealing performance (airtightness) and durability can be provided.

The linear expansion coefficient of the bonding material is generally dependent on that of the main component, and can be adjusted by mixing the main component with other additive(s). In order to control the linear expansion coefficient to be $30\times10^{-7}$/K to $90\times10^{-7}$/K, it is preferred to use alumina, zirconia, silica, graphite, $P_2O_5$, $Bi_2O_3$, SnO, or the like as the main component.

As the bonding material, a commercially available product may be used as well, and examples thereof include: "TB3732" manufactured by ThreeBond Holdings Co., Ltd.; "ARON CERAMIC D" and "ARON CERAMIC E", which are manufactured by Toagosei Co., Ltd.; "FP-74", "KP312E", "FP-67", "BNL115BB", "ASF-1094", "ASF-1098" and "ASF-1109", which are manufactured by AGC Inc.; and "CERAMABOND 552" manufactured by Aremco Products Inc.

The dense member bonded to the alcohol-selective permeable membrane with the bonding material is a member which has a denseness (airtightness) at a level that a gas used for a reaction and a reacted gas do not leak from the member, and examples of the dense member include a cap that seals an end of a tubular member, and a pipe connected with an end of a tubular member. The dense member is not particularly restricted as long as it has such a denseness, and a metal is typically used. Examples of the metal include: SUS materials made of stainless steel; ceramics, such as alumina and zirconia; and alloys, such as kovar.

In the present embodiment, the dense member has a linear expansion coefficient of preferably $30\times10^{-7}$ 1 K or more and $200\times10^{-7}$/K or less. When the linear expansion coefficient of the dense member is in this range, a difference thereof from the linear expansion coefficient of the bonding material is small, so that good sealing airtightness and durability can be maintained.

The difference in linear expansion coefficient between the bonding material and the dense member is preferably $50\times10^{-7}$/K or smaller, more preferably $40\times10^{-7}$/K or smaller, still more preferably $30\times10^{-7}$/K or smaller. When the difference in linear expansion coefficient between the bonding material and the dense member is small in this manner, bonding defects caused by shrinkage of a material during sintering of the bonding material can be inhibited.

The alcohol-selective permeable membrane of the present embodiment is typically a zeolite membrane; however, it is not particularly restricted as long as it can selectively allow alcohol to permeate therethrough and, for example, various porous membranes and MOFs (Metal Organic Frameworks) can be used as well.

In one mode, the zeolite membrane is formed on a porous support member made of alumina or the like, and used as a zeolite membrane complex.

A zeolite mainly constituting the zeolite membrane is preferably one which contains a zeolite having a pore structure of 6- to 12-membered oxygen ring.

The value n of the above-described zeolite having an n-membered oxygen ring indicates the number of oxygen atoms in a pore having the largest number of oxygen atoms among the pores formed by oxygen constituting a zeolite skeleton and T elements (elements other than oxygen constituting the skeleton). For example, when pores of 12-membered oxygen rings and pores of 8-membered rings exist as in the case of an MOR-type zeolite, the zeolite is considered to have a 12-membered oxygen ring.

Examples of the zeolite having a pore structure of 6- to 12-membered oxygen ring include, in terms of the codes defined by the International Zeolite Association (IZA): AEI, AEL, AFI, AFG, ANA, ATO, BEA, BRE, CAS, CDO, CHA, CON, DDR, DOH, EAB, EPI, ERI, ESV, EUO, FAR, FAU, FER, FRA, HEU, GIS, GIU, GME, GOO, ITE, KFI, LEV, LIO, LOS, LTA, LTL, LTN, MAR, MEP, MER, MEL, MFI, MON, MOR, MSO, MTF, MTN, MTW, MWW, NON, NES, OFF, PAU, PHI, RHO, RTE, RTH, RUT, SGT, OD, STI, STT, TOL, TON, TSC, UFI, VNI, WEI, and YUG. The zeolite is preferably any one selected from these zeolites.

The zeolite particularly suitably used in the present embodiment is preferably one which selectively adsorbs alcohol. The zeolite is more preferably able to selectively adsorb a target substance by the zeolite for the purpose of, for example, allowing large-sized molecules to permeate therethrough or separating molecules of comparable sizes from one another, rather than as a simple molecular sieve, namely for the purpose of allowing molecules to permeate therethrough, simply based on molecular size differences. In other words, a zeolite that separates molecules based on selective adsorption thereof to the zeolite surface is more preferred. The selective adsorption capacity of such zeolite is decreased when the temperature is increased; therefore, the effects of the present invention are more prominently exerted.

The ease of alcohol adsorption is strongly influenced by the molar ratio Si/Al in the zeolite. The molar ratio Si/Al in the zeolite is usually 2 or higher, preferably 4 or higher, but usually 100 or lower, preferably 50 or lower. When the molar ratio Si/Al is low, the crystal stability is decreased, making the synthesis difficult. Meanwhile, when the molar ratio Si/Al is high, alcohol is less likely to adsorb, as a result of which the separation performance is not sufficiently exerted.

The molar ratio Si/Al in the zeolite can be determined by a generally known analysis method. Examples thereof include: a method of dissolving zeolite and measuring the molar ratio by ICP (inductively-coupled plasma emission spectroscopy); a method of measuring the molar ratio directly in a solid state by EDX (energy dispersive X-ray spectroscopy); and a method of measuring the molar ratio by a combination of ion-beam sputtering and XPS (X-ray photoelectron spectroscopy), and an appropriate method can be selected in accordance with the shape of the membrane and the material of the support.

A zeolite is poor in flexibility; therefore, when it is made into a membrane, the membrane is produced in the form of being supported on a substrate. A support is a porous such that gas molecules can penetrate thereinto and, for example, the support has a large number of three-dimensionally connected fine small holes.

A material constituting the support is preferably chemically stable enough not to react with an untreated gas, and preferably has excellent mechanical strength. Specifically, various oxide ceramics, such as alumina, silica, silica-alumina, mullite, cordierite and zirconia, as well as silicon carbide, carbon, and glass can be used.

The shape of the support varies depending on the intended use of the zeolite membrane; however, particularly, a zeolite membrane on a cylindrical support is strong against a pressure from the outside, and is thus suitable for the simple use in a batch process, a circulation process (recycle process), and the like.

In the present embodiment, a zeolite membrane complex in which a zeolite membrane is formed on a support can be used. The zeolite membrane complex is obtained by, for example, preparing a cylindrical support and, first, supporting zeolite microcrystals inside its pores. As a supporting method, for example, a dipping method, a rubbing method, a suction method, or an impregnation method can be employed. The microcrystals, which play a role as nuclei for the growth of crystals constituting the zeolite membrane, are also referred to as "seed crystals". For the growth of zeolite, hydrothermal synthesis can be employed in the same manner as in the zeolite synthesis.

The thickness of the zeolite membrane in the zeolite membrane complex is not particularly restricted; however, it is usually 0.1 µm or greater, preferably 0.5 µm or greater, but usually 50 µm or less, preferably 20 µm or less. By controlling the thickness of the zeolite membrane to be a certain value or greater, a sufficient denseness is obtained, and the selectivity of the membrane is maintained high. Further, by controlling the thickness of the zeolite membrane to be a certain value or less, a sufficient gas permeation amount is obtained.

On the catalyst layer in the reactor, the heat recovery means and the alcohol-selective permeable membrane can be installed in the entire region from the upstream to the downstream along the flow of the raw material gas. Alternatively, an upstream portion may be provided only with the heat recovery means, while a downstream portion may be provided with both the alcohol-selective permeable membrane and the heat recovery means.

The reactor may have a single reactor chamber, or two or more separated reactor chambers. When there are two or more reaction chambers, the heat recovery means and the alcohol-selective permeable membrane may be installed in all of the reaction chambers. Alternatively, the alcohol-selective permeable membrane may be installed only in a reaction chamber on the downstream side, not in a reaction chamber on the upstream side. When a reaction chamber is divided into two or more reaction chambers, the heat recovery means does not have to be installed in the reaction chamber having a small amount of heat generation.

As a method of using the heat recovered by the heat recovery means as a heat source for a process, a condensed component may be recovered from an outlet gas on the non-permeation side and/or the permeation side, and non-condensed raw materials may be subsequently recycled to the upstream of the reactor.

The installation area of the alcohol-selective permeable membrane in the reactor is represented by A/V (m$^2$/m$^3$), which is a ratio of the membrane area (A) per unit catalyst volume (V).

The catalyst volume refers to a filling volume (m$^3$) of the catalyst in the reactor, and is a value obtained by dividing the catalyst weight (kg) by the bulk density (kg/m$^3$).

The membrane area (m$^2$) is a macroscopically apparent area of the alcohol-selective permeable membrane installed in the reactor. For example, in the case of a square flat plate-type alcohol-selective permeable membrane, it is approximated to a cuboid and, in this approximated cuboid, the area (length×width) of the surface having the alcohol-selective permeable membrane is defined as the membrane area. Further, in the case of a cylindrical alcohol-selective permeable membrane, it is approximated to a cylinder, and the side surface area of this cylinder (diameter×π×height) is defined as the membrane area.

When the reactor is divided into plural reactors, the catalyst volume and the membrane area are a sum of the values in all of the reactors, respectively. The value of the membrane area per unit catalyst volume A/V is usually 5 or larger, preferably 10 or larger, but usually 150 or smaller, preferably 120 or smaller. When the value of the membrane area per unit catalyst volume A/V is too small, an effect of improving the conversion rate by the alcohol-selective permeable membrane is not sufficiently obtained, whereas when this value is too large, the apparatus cost is increased.

The separation selectivity of the alcohol-selective permeable membrane is represented by a permeability coefficient ratio between a separation target substance and a separation non-target substance. The permeability coefficient is the amount (mol) of a permeable substance per unit membrane area (m$^2$), unit differential pressure (Pa), and unit time (s). The term "differential pressure (Pa)" used herein refers to the difference in partial pressure of a substance between the non-permeation side and the permeation side of a membrane.

The term "permeability coefficient ratio" used herein refers to a value obtained by dividing the permeability coefficient of a separation target substance measured at the same temperature as a process by the permeability coefficient of a separation non-target substance measured at the same temperature as the process.

The permeability coefficient ratio of alcohol and hydrogen (alcohol/hydrogen) is usually 10 or higher, preferably 20 or higher, more preferably 50 or higher. When the permeability coefficient ratio of alcohol and hydrogen is too low, the loss of the raw materials to the permeation side and the amount of recycled gas are increased, as a result of which the energy consumption is increased.

(Description of Production Method)

Another embodiment of the present invention is an alcohol production method, including the synthesis step of synthesizing an alcohol by allowing raw materials, which contain at least hydrogen and carbon monoxide and/or carbon dioxide, to react in the presence of a catalyst, wherein the method further includes: the separation-recovery step of separating and recovering the thus obtained alcohol in a reactor using a zeolite-containing alcohol-selective permeable membrane; and the heat recovery step of recovering at least some of reaction heat generated in the synthesis step from the reactor, and the separation-recovery step and the heat recovery step are carried out concurrently.

In the present embodiment, the raw material, the catalyst, the alcohol-selective permeable membrane, the reactor and the like to be used may be the above-described ones. In the present embodiment, a raw material gas, which contains at least hydrogen and carbon monoxide and/or carbon dioxide, is allowed to react in the presence of a catalyst in a reactor, whereby an alcohol is obtained. The reaction conditions are not particularly restricted; however, the reaction temperature is usually 200° C. or higher, preferably 210° C. or higher, more preferably 220° C. or higher, but usually 300° C. or lower, preferably 290° C. or lower, more preferably 270° C. or lower. The reaction temperature may be any combination of these upper limit values and lower limit values. It is noted here that the reaction temperature means the gas temperature inside the reactor. By controlling the reaction temperature to be not lower than the above-described lower limit, the reaction rate is increased, so that the productivity is improved. By controlling the reaction temperature to be not higher than the above-described upper limit, the chemical equilibrium of the reaction is made advantageous for obtaining an alcohol; therefore, a high conversion rate can be attained even when the membrane performance is somewhat deteriorated. In addition, the acceptable range of the heat resistance required for a bonding material is widened.

The alcohol obtained by the above-described reaction permeates through the alcohol-selective permeable membrane in the reactor and is recovered from a permeated gas outlet of the reactor in the separation-recovery step. In addition, the heat recovery step of recovering at least some of the reaction heat generated in the alcohol synthesis from the reactor is carried out concurrently with the separation-recovery step.

The alcohol production method may also include the supply step of supplying at least some of the reaction heat recovered in the heat recovery step for heating at least one raw material selected from hydrogen, carbon monoxide and carbon dioxide before the raw material is introduced into the reactor. The recovered reaction heat may be used for other application as well.

The pressure in the reactor when allowing the generated alcohol to permeate through the alcohol-selective permeable membrane, namely the pressure (gauge pressure) on the gas supply side of the alcohol-selective permeable membrane in the reactor, is preferably 1 MPaG or higher, more preferably 2 MPaG or higher, but preferably 8 MPaG or lower, more preferably 5 MPaG or lower. By controlling the pressure in an appropriate range, the equilibrium constrain of the reaction is reduced and the reaction rate is increased, so that a higher productivity is likely to be achieved. In addition, an increase in the production cost of the reactor and an increase in the cost for increasing the pressure of the raw material gas, due to an excessively high pressure, can be inhibited.

Further, in the reactor, the alcohol partial pressure (absolute pressure) on the gas supply side of the alcohol-selective permeable membrane is preferably 0.1 MPaA or higher, more preferably 0.2 MPaA or higher, but preferably 6 MPaA or lower, more preferably 5 MPaA or lower. By controlling the alcohol partial pressure in this range, the alcohol permeating through the membrane is obtained in a sufficient amount, and the effect of the membrane is exerted favorably. In addition, with the alcohol partial pressure being in this range, the durability and the airtightness that are required for a bonded part are not excessively high more than necessary, and bonding can thus be carried out easily and in a large amount.

The gauge pressure in the reactor can be measured using a pressure gage provided in the reactor. The absolute pressure of the alcohol in the reactor varies from the upstream to the downstream of the reactor; however, in the present embodiment, a value calculated from the results of analyzing the composition of the reactor outlet gas by gas chromatography and the gauge pressure is defined as the absolute pressure of the alcohol in the reactor.

EXAMPLES

The present invention will now be described more concretely by way of Examples thereof; however, the present invention is not restricted to the following Examples within the gist thereof. Various measurements and evaluations in Examples were performed as described below.
<Thermal Expansion Coefficient of Inorganic Glass and Dense Member>

With regard to the thermal expansion coefficient (linear expansion coefficient) of an inorganic glass frit and that of a dense member at 30 to 250° C., a columnar test piece of about 5 mm in diameter and about 10 to 20 mm in length is prepared from a sample, the expansion amount of this test piece in the above-described temperature range is measured using a differential thermal expansion meter (TMA8310, manufactured by Rigaku Corporation), and the average linear expansion coefficient is calculated. In the present Examples, catalog values or manufacturer report values were used.
<Softening Point of Inorganic Glass>

The softening point is measured using a differential thermal analyzer (TG8120, manufactured by Rigaku Corporation). A glass frit pulverized using a mortar is heated at a rate of 10° C./min, and a second inflection point of the thus obtained DTA curve is defined as the softening point.

As the values stated in the present Examples, catalog values or manufacturer report values were used.
<Measurement of Air Permeation Amount>

One end (the end not bonded with a cap) of a subject bonded body in an airtightly maintained state was connected to a 5-kPa vacuum line under atmospheric pressure, and the flow rate of the air permeating through a zeolite membrane complex was measured using a mass flow meter arranged between the vacuum line and the bonded body. It is noted here that "sccm" represents "cc/min" at 0° C. and 1 atm. As the mass flow meter, GF40 (maximum flow rate: 20 sccm) manufactured by Brooks Instrument was used.
<Durability Test>

The bonded bodies obtained in Examples and Comparative Examples were each placed in an SUS-316 autoclave having an inner volume of 80 ml, and 5 ml of methanol and 5 ml of desalted water were added thereto, after which the autoclave was hermetically sealed and set in an electric furnace, and this electric furnace was heated to 280° C. by 1 hour. At this point, the pressure inside the autoclave was 3.5 MPa. The heating was terminated 48 hours after the temperature reached 280° C., and the autoclave was taken out of the electric furnace and naturally cooled. After being cooled for at least 2 hours, the autoclave was opened to take out the bonded body. The bonded body was dried at 120° C. for 4 hours under normal pressure, and the above-described measurement of air permeation amount was performed thereafter.

First, concrete examples are presented regarding the first and the second embodiments.

Example A1

(Preparation of Complex of Zeolite and Alumina Porous Support)

A cylindrical alumina porous support (outer diameter: 12 mm, inner diameter: 9 mm, total length: 40 mm) to which seed crystals had been adhered in advance was vertically immersed in a TEFLON (registered trademark)-made inner cylinder containing an aqueous reaction mixture having a composition (molar ratio) of $SiO_2:Na_2O:Al_2O_3:H_2O=100:27.8:0.021:4,000$, and an autoclave was hermetically sealed to perform hydrothermal synthesis at 180° C. for 12 hours. After a prescribed time, the autoclave was cooled to normal temperature, and the resulting porous support-zeolite complex was taken out of the reaction mixture, washed, and then dried at 120° C. for at least 4 hours, whereby a complex of MFI-type zeolite and alumina porous support was obtained.
(Production of Bonded Body)

As a lead-free inorganic glass, 0.3 g of a glass frit "FP-74" manufactured by AGC Inc. (thermal expansion coefficient: $63 \times 10^{-7}$/K, softening point: 355° C., SnO content: 42%) was filled into a recess of a kovar-made cap (thermal expansion coefficient: $52\times10^{-7}$/K, outer diameter: 14.0 mm, inner diameter: 12.2 mm, height: 4 mm), and the above-obtained complex of MFI-type zeolite and alumina porous support was placed thereon. Subsequently, the complex was placed in a muffle furnace with a 560-g weight being placed on top of the complex to apply a load. The complex was heated to 480° C. by 100 minutes, and then fired by maintaining this 480° C. state for 30 minutes. Thereafter, the heating was terminated, and the resultant was naturally cooled to obtain a bonded body.

For the thus obtained bonded body, the air permeation amount was measured and the durability test was conducted. As a result, the air permeation amount of the bonded body before the durability test was found to be 0.1 sccm or less. Further, it was found that the bonded body exhibited good durability as its air permeation amount after the durability test was 0.1 sccm or less with no change before and after the test.

Example A2

A bonded body was obtained in the same manner as in Example A1, except that a glass fit "KP312E" manufactured by AGC Inc. (thermal expansion coefficient: $71\times10^{-7}$/K, softening point: 344° C., SnO content: 52%) was used as the inorganic glass, and the firing temperature in the muffle furnace was changed to 430° C.

For the thus obtained bonded body, the air permeation amount was measured and the durability test was conducted. As a result, the air permeation amount of the bonded body before the durability test was found to be 0.1 sccm or less. Further, it was found that the bonded body exhibited good durability as its air permeation amount after the durability test was 0.1 sccm or less with no change before and after the test.

Example A3

A bonded body was obtained in the same manner as in Example A1, except that a glass fit "FP-67" manufactured by AGC Inc. (thermal expansion coefficient: $79\times10^{-7}$/K, softening point: 357° C., SnO content: 50%) was used as the inorganic glass.

For the thus obtained bonded body, the air permeation amount was measured. As a result, the air permeation amount of the bonded body was found to be 0.1 sccm or less.

Example A4

A bonded body was obtained in the same manner as in Example A1, except that a glass fit "BNL115BB" manufactured by AGC Inc. (thermal expansion coefficient: $74\times10^{-7}$/K, softening point: 397° C., $B_2O_3$ content: 5.0%) was used as the inorganic glass, and the firing temperature in the muffle furnace was changed to 500° C.

For the thus obtained bonded body, the air permeation amount was measured and the durability test was conducted. As a result, the air permeation amount of the bonded body before the durability test was found to be 0.4 sccm. The air permeation amount of the bonded body after the durability test was also 0.4 sccm, showing no change in the airtightness.

Example A5

A sealing treatment was performed on the bonded body of Example A4. Specifically, the bonded part between the complex of MFI-type zeolite and alumina porous support and the cap was coated with a methyl silicate oligomer "MKC SILICATE (registered trademark) MS-56" manufactured by Mitsubishi Chemical Corporation while reducing the pressure inside. This bonded body was left at room temperature for 1 hour, and subsequently heat-treated at 250° C. for 30 minutes to complete the sealing treatment.

For the thus obtained bonded body, the air permeation amount was measured and the durability test was conducted. As a result, it was found that the air permeation amount of the bonded body before the durability test was 0.1 sccm or less, indicating that the airtightness was improved by the sealing treatment. It was also found that the bonded body exhibited good durability as its air permeation amount after the durability test was 0.1 sccm or less with no change before and after the test.

Example A6

A bonded body was obtained in the same manner as in Example A1, except that a glass fit "BF-0606" manufactured by Nippon Electric Glass Co., Ltd. (thermal expansion coefficient: $72\times10^{-7}$/K, softening point: 450° C., $B_2O_3$ content: 6.4%) was used as the inorganic glass, and the firing temperature in the muffle furnace was changed to 485° C.

For the thus obtained bonded body, the air permeation amount was measured and the durability test was conducted. As a result, the air permeation amount of the bonded body before the durability test was found to be 0.2 sccm. The air permeation amount of the bonded body after the durability test was also 0.2 sccm, showing no change in the airtightness.

Example A7

A bonded body was obtained in the same manner as in Example A1, except that a glass fit "BF-0901" manufactured by Nippon Electric Glass Co., Ltd. (thermal expansion coefficient: $48\times10^{-7}$/K, softening point: 528° C., $B_2O_3$ content: 9.7%) was used as the inorganic glass, and the firing temperature in the muffle furnace was changed to 560° C.

For the thus obtained bonded body, the air permeation amount was measured and the durability test was conducted. As a result, the air permeation amount of the bonded body before the durability test was found to be 0.1 sccm or less. Further, it was found that the bonded body exhibited good durability as its air permeation amount after the durability test was 0.1 sccm or less with no change before and after the test.

Example A8

A bonded body was obtained in the same manner as in Example A1, except that a glass fit "ASF-1094" manufactured by AGC Inc. (thermal expansion coefficient: $79\times10^{-7}$/K, softening point: 533° C., $B_2O_3$ content: 15%) was used as the inorganic glass, and the firing temperature in the muffle furnace was changed to 550° C.

For the thus obtained bonded body, the air permeation amount was measured and the durability test was conducted. As a result, the air permeation amount of the bonded body before the durability test was found to be 0.3 sccm. The air permeation amount of the bonded body after the durability test was also 0.3 sccm, showing no change in the airtightness.

Example A9

A bonded body was obtained in the same manner as in Example A1, except that a glass fit "ASF-1098" manufactured by AGC Inc. (thermal expansion coefficient: 54×10⁻⁷1 K, softening point: 515° C., B$_2$O$_3$ content: 16%) was used as the inorganic glass, and the firing temperature in the muffle furnace was changed to 560° C.

For the thus obtained bonded body, the air permeation amount was measured. As a result, the air permeation amount of the bonded body was found to be 0.7 sccm.

Example A10

A bonded body was obtained in the same manner as in Example A1, except that a glass fit "ASF-1109" manufactured by AGC Inc. (thermal expansion coefficient: 65×10⁻⁷/K, softening point: 545° C., B$_2$O$_3$ content: 19%) was used as the inorganic glass, and the firing temperature in the muffle furnace was changed to 560° C.

For the thus obtained bonded body, the air permeation amount was measured. As a result, the air permeation amount of the bonded body was found to be 1.2 sccm.

Comparative Example A1

A bonded body was obtained in the same manner as in Example A1, except that a glass fit "SK-231-300" manufactured by AGC Inc. (thermal expansion coefficient: 84×10⁻⁷/K, softening point: 559° C., B$_2$O$_3$ content: 13%) was used as the inorganic glass, and the firing temperature in the muffle furnace was changed to 580° C.

For the thus obtained bonded body, the air permeation amount was measured. As a result, the air permeation amount of the bonded body was found to be 5.5 sccm.

Comparative Example A2

A bonded body was obtained in the same manner as in Example A1, except that a glass fit "KF9173" manufactured by AGC Inc. (thermal expansion coefficient: 98×10⁻⁷/K, softening point: 462° C., B$_2$O$_3$ content: 11%) was used as the inorganic glass, and the firing temperature in the muffle furnace was changed to 520° C.

For the thus obtained bonded body, the air permeation amount was measured and the durability test was conducted. As a result, the air permeation amount of the bonded body before the durability test was found to be 7.3 sccm. Further, it was found that the airtightness was deteriorated as the air permeation amount of the bonded body after the durability test was 20 sccm or larger (over the measurement range).

Next, concrete examples are presented regarding the third embodiment in which an inorganic adhesive is used as a bonding material.

Example B1

(Preparation of Complex of Zeolite and Alumina Porous Support)

An alumina porous support (outer diameter: 12 mm, inner diameter: 9 mm, total length: 40 mm) to which seed crystals had been adhered in advance was vertically immersed in a TEFLON (registered trademark)-made inner cylinder containing an aqueous reaction mixture having a composition of SiO$_2$:Na$_2$O:Al$_2$O$_3$:H$_2$O=100:27.8:0.021:4,000, and an autoclave was hermetically sealed to perform hydrothermal synthesis at 180° C. for 12 hours. After a prescribed time, the autoclave was cooled to normal temperature, and the resulting porous support-zeolite complex was taken out of the reaction mixture, washed, and then dried at 120° C. for at least 4 hours, whereby a complex of MFI-type zeolite and alumina porous support was obtained.

(Production of Bonded Body)

As an inorganic adhesive, 0.6 g of "TB3732" manufactured by ThreeBond Holdings Co., Ltd. (alumina-based, post-curing thermal expansion coefficient: 80×10⁻⁷/K, containing a metal alkoxide) was filled into a recess of a kovar-made cap (outer diameter: 14.0 mm, inner diameter: 12.2 mm, height: 4 mm, thermal expansion coefficient: 52×10⁻⁷/K), and the above-obtained complex of MFI-type zeolite and alumina porous support was placed thereon. Subsequently, a 560-g weight was placed on top of the complex to apply a load, and the complex was left at room temperature for 1 hour. Thereafter, the complex was heated at 100° C. for 30 minutes and then naturally cooled to obtain a bonded body.

Example B2

A sealing treatment was performed on the bonded body of Example 1. Specifically, the bonded part between the complex of MFI-type zeolite and alumina porous support and the cap was coated with a methyl silicate oligomer "MKC SILICATE (registered trademark) MS-56" manufactured by Mitsubishi Chemical Corporation while reducing the pressure inside. This bonded body was left at room temperature for 1 hour, and subsequently heat-treated at 250° C. for 30

TABLE 1

| | Thermal expansion coefficient (×10⁻⁷/° C.) | Softening point | SnO (% by mass) | B$_2$O$_3$ (% by mass) | Firing temperature (° C.) | Sealing treatment | Air permeation amount (sccm) | Air permeation amount after durability test (sccm) |
|---|---|---|---|---|---|---|---|---|
| Example A1 | 63 | 355 | 42 | — | 480 | — | ≤0.1 | ≤0.1 |
| Example A2 | 71 | 344 | 52 | — | 430 | — | ≤0.1 | ≤0.1 |
| Example A3 | 79 | 357 | 50 | — | 480 | — | ≤0.1 | |
| Example A4 | 74 | 397 | — | 5.0 | 500 | — | 0.4 | ≤0.4 |
| Example A5 | 74 | 397 | — | 5.0 | 500 | Silicate oligomer treatment | ≤0.1 | ≤0.1 |
| Example A6 | 72 | 450 | — | 6.4 | 485 | — | 0.2 | 0.2 |
| Example A7 | 48 | 528 | — | 9.7 | 560 | — | ≤0.1 | ≤0.1 |
| Example A8 | 79 | 533 | — | 15 | 550 | — | 0.3 | 0.3 |
| Example A9 | 54 | 515 | — | 16 | 560 | — | 0.7 | |
| Example A10 | 65 | 545 | — | 19 | 560 | — | 1.2 | |
| Comparative Example A1 | 84 | 559 | — | 13 | 580 | — | 5.5 | |
| Comparative Example A2 | 98 | 462 | — | 11 | 520 | — | 7.3 | ≥20 | minutes to form a sealing film. The air permeation amount was measured to be 0.1 sccm or less, indicating that the sealing performance was improved by the sealing film.

Example B3

As an inorganic adhesive, 0.6 g of "ARON CERAMIC D" manufactured by Toagosei Co., Ltd. (alumina-based, post-curing thermal expansion coefficient: $80 \times 10^{-7}$/K, not containing a metal alkoxide) was loaded, and the above-obtained complex of MFI-type zeolite and alumina porous support was placed thereon. Subsequently, a 560-g weight was placed on top of the complex to apply a load, and the complex was left at room temperature for 20 hours. Thereafter, the complex was heated at 90° C. for 1 hour and then at 150° C. for 1 hour, after which the complex was naturally cooled to obtain a bonded body. The air permeation amount was measured to be 14 sccm.

Example B4

A bonded body subjected to a sealing treatment was obtained in the same manner as in Example 2, except that the bonded body of Example B3 was used. The air permeation amount was measured to be 0.1 sccm or less, indicating that the sealing performance was improved by the sealing treatment.

Example B5

A bonded body was obtained in the same manner as in Example B3, except that "ARON CERAMIC E" manufactured by Toagosei Co., Ltd. (zirconia silica-based, post-curing thermal expansion coefficient: $40 \times 10^{-7}$/K, not containing a metal alkoxide) was used as the inorganic adhesive. The air permeation amount was measured to be 18 sccm.

Example B6

A bonded body subjected to a sealing treatment was obtained in the same manner as in Example B2, except that the bonded body of Example B5 was used. The air permeation amount was measured to be 0.1 sccm or less, indicating that the sealing performance was improved by the sealing film.

Example B7

A bonded body subjected to a sealing treatment was obtained in the same manner as in Example B2, except that "PERMEATE HS-90" manufactured by D&D Corporation was used in place of the methyl silicate oligomer "MKC SILICATE (registered trademark) MS-56" manufactured by Mitsubishi Chemical Corporation. The air permeation amount was measured to be 0.1 sccm or less, indicating that the sealing performance was improved by the sealing film.

Comparative Example B1

A bonded body was obtained in the same manner as in Example B3, except that "ARON CERAMIC C" manufactured by Toagosei Co., Ltd. (silica-based, post-curing thermal expansion coefficient: $130 \times 10^{-7}$/K, not containing a metal alkoxide) was used as the inorganic adhesive. The air permeation amount was measured to be 103 sccm.

The results of Examples B1 to B7 and Comparative Example B1 are shown in Table 2.

TABLE 2

| | Inorganic adhesive | Thermal expansion coefficient ($\times 10^{-7}$/K) | Metal alkoxide | Sealing treatment | Air permeation amount immediately after bonding (sccm) |
|---|---|---|---|---|---|
| Example B1 | TB3732 (Almina-based) | 80 | contained | not performed | 0.3 |
| Example B2 | TB3732 (Almina-based) | 80 | contained | performed (MS-56) | 0.1 or less |
| Example B3 | ARON CERAMIC D (Almina-based) | 80 | not contained | not performed | 14 |
| Example B4 | ARON CERAMIC D (Almina-based) | 80 | not contained | performed (MS-56) | 0.1 or less |
| Example B5 | ARON CERAMIC E (Zirconia-silica-based) | 40 | not contained | not performed | 18 |
| Example B6 | ARON CERAMIC E (Zirconia-silica-based) | 40 | not contained | performed (MS-56) | 0.1 or less |
| Example B7 | TB3732 (Almina-based) | 80 | contained | performed (HS90) | 0.1 or less |
| Comparative Example B1 | ARON CERAMIC C (Silica-based) | 130 | not contained | not performed | 103 |

Example B8

(Durability Test)

The bonded body of Example B1 was placed in an SUS-316 autoclave having an inner volume of 80 ml, and 5 ml of methanol and 5 ml of desalted water were added thereto, after which the autoclave was hermetically sealed under atmospheric pressure and set in an electric furnace, and this electric furnace was heated to 280° C. by 1 hour. Heating was terminated 48 hours after the temperature reached 280° C. (the pressure was 3.2 MPaG at this point), and the autoclave was taken out of the electric furnace and naturally cooled. After being cooled for at least 2 hours, the autoclave was opened to take out the bonded body. The bonded body was dried at 120° C. for 4 hours under normal pressure and, when the air permeation amount was subsequently measured, it was found to be 0.3 sccm with no change before and after the test, indicating that the bonded body exhibited good durability.

Example B9

A durability test was conducted in the same manner as in Example B8, except that the bonded body of Example B2 was used. The air permeation amount was 0.1 sccm or less.

Example B10

A durability test was conducted in the same manner as in Example B8, except that the bonded body of Example B7 was used. The air permeation amount was 0.2 sccm.

Comparative Example B2

A durability test was conducted in the same manner as in Example B8, except that the bonded body of Comparative Example B1 was used. The air permeation amount was 300 sccm or larger (over the measurement range).

Comparative Example B3

A bonded body was obtained in the same manner as in Example B1, except that "TB1208B" manufactured by ThreeBond Holdings Co., Ltd. (silicone-based, not containing a metal alkoxide) was used as an adhesive different from the inorganic adhesive, and the heating was performed at 120° C. for 1 hour instead of at 100° C. for 30 minutes. The air permeation amount was measured to be 0.1 sccm or less. When a durability test was conducted using this bonded body in the same manner as in Example B7, it was found that the bonded part was broken, and the complex of MFI-type zeolite and alumina porous support was separated from the cap.

Results of Examples B8 to B10 and Comparative Examples B2 and B3 are shown in Table 3.

least 4 hours, whereby a complex of MFI-type zeolite and alumina porous support (hereinafter, referred to as "membrane complex") was obtained. The thus obtained membrane complex was cut as required for use.

A kovar-made cap (linear expansion coefficient: $52 \times 10^7$/K) and a kovar-made connecting pipe (linear expansion coefficient: $52 \times 10^7$/K) were bonded to the membrane complex using a glass frit "BNL115BB" manufactured by AGC Inc. (post-firing linear expansion coefficient: $74 \times 10^7$/K) by firing in a muffle furnace at 500° C. for 30 minutes. The membrane complex had an effective membrane length of 34 mm after the bonding.

<Production of Methanol>

Methanol was produced using a fixed-bed reactor made of SUS316L (inner volume: 120 mL). The kovar-made connecting pipe bonded to the membrane complex was connected to the reactor using a SWAGELOK (registered trademark) union. The periphery of the membrane complex was filled with 75 g of a Cu—Zn composite oxide catalyst F07J (containing 49% by weight of CuO, 45% by weight of ZnO, and 5.6% by weight of $Al_2O_3$) manufactured by JGC Catalysts and Chemicals Ltd., and the reactor was hermetically sealed.

Before carrying out a reaction, $H_2$ diluted with $N_2$ ($H_2$/$N_2$=25/75, molar concentration) was circulated in the reactor at 100 mL/min, and the catalyst was reduced at 300° C. under normal pressure for 6 hours.

After the completion of this catalyst reduction, the reactor was allowed to cool, and the circulating gas was subsequently changed to a syngas (raw material gas: $H_2$/CO=66.9/33.1, molar ratio, 332 mL/min), to carry out the reaction with membrane separation at a reactor temperature of 250° C. and a reactor internal pressure of 3 MPaG. The methanol partial pressure in the reactor was 0.55 MPaA.

TABLE 3

| | Inorganic adhesive | Thermal expansion coefficient ($\times 10^{-7}$/K) | Metal alkoxide | Sealing treatment | Air permeation amount immediately after bonding (sccm) |
|---|---|---|---|---|---|
| Example B8 | TB3732 (Almina-based) | 80 | contained | not performed | 0.3 |
| Example B9 | TB3732 (Almina-based) | 80 | contained | performed (MS-56) | 0.1 or less |
| Example B10 | TB3732 (Almina-based) | 80 | contained | performed (HS-90) | 0.2 |
| Comparative Example B2 | ARON CERAMIC C (Silica-based) | 130 | not contained | not performed | 300 or more |
| Comparative Example B3 | TB1208B (Silicone-based) | — | not contained | not performed | Breakage of bonded part |

Next, concrete examples are presented regarding the fourth embodiment of the present invention.

Example C1

An alumina porous support to which seed crystals had been adhered in advance was vertically immersed in a TEFLON (registered trademark)-made inner cylinder containing an aqueous reaction mixture having a composition of $SiO_2$:$Na_2O$:$Al_2O_3$:$H_2O$=100:27.8:0.021:4,000, and an autoclave was hermetically sealed to perform hydrothermal synthesis at 180° C. for 12 hours. After a prescribed time, the autoclave was cooled to normal temperature, and the resulting porous support-zeolite complex was taken out of the reaction mixture, washed, and then dried at 120° C. for at The resulting gaseous product was analyzed by on-line gas chromatography using $N_2$ as an internal standard substance for both membrane non-permeable components and membrane permeable components. After the analysis result was stabilized, the $CO_x$ conversion rate was calculated by the following Formula 4.

$CO_x$ conversion rate=1−(non-permeated gas outlet CO flow rate+non-permeated gas outlet $CO_2$ flow rate+permeated gas outlet CO flow rate+permeated gas outlet $CO_2$ flow rate)/(raw material feed inlet CO flow rate+raw material feed inlet $CO_2$ flow rate)  Formula 4:

Further, the equilibrium $CO_x$ conversion rate was determined from the equilibrium of the methanol synthesis reaction represented by the following Formulae 1 and 2, and the value of CO$_x$ conversion rate/equilibrium CO$_x$ conversion rate was determined as an index indicating the rate of increase in the conversion rate from the equilibrium conversion rate.

$$3H_2 + CO_2 \leftarrow\rightarrow CH_3OH + H_2O \quad \text{Formula 1:}$$

$$2H_2 + CO \leftarrow\rightarrow CH_3OH \quad \text{Formula 2:}$$

Example C2

As Example C2, the same procedures were performed as in Example C1, except that the reactor internal pressure was changed to 1.5 MPaG The methanol partial pressure in the reactor was 0.33 MPaA.

Example C3

As Example C3, the same procedures were performed as in Example C1, except that the temperature in the reactor was changed to 230° C., and the raw material gas flow rate was changed to 83 mL/min. The methanol partial pressure in the reactor was 0.87 MPaA.

Example C4

A membrane complex of another lot that was synthesized under the same conditions as in Example C1, a kovar-made cap, and a connecting pipe were bonded in the same manner as in Example C1, except that a glass frit "FP-74" manufactured by AGC Inc. (post-firing linear expansion coefficient: 63×10$^7$/K) was used for the bonding, and the firing temperature was changed to 480° C. The membrane complex had an effective membrane length of 38 mm after the bonding.

As Example C4, methanol was produced in the same manner as in Example C1, except that the catalyst amount was set at 75 g, and the circulated raw material gas was changed to a CO$_2$-containing syngas (H$_2$/CO/CO$_2$=69.5/23.2/7.3, molar ratio, 147 mL/min). The methanol partial pressure in the reactor was 0.71 MPaA.

Example C5

As Example C5, the same procedures were performed as in Example C4, except that the composition of the circulated gas was changed to H$_2$/CO$_2$=75/25 (molar ratio), and the flow rate was changed to 131 mL/min. The methanol partial pressure in the reactor was 0.22 MPaA.

Example C6

A membrane complex of another lot that was synthesized under the same conditions as in Example C1, a kovar-made cap, and a connecting pipe were bonded using an inorganic adhesive "CERAMABOND 552" manufactured by Aremco Products Inc. (post-firing linear expansion coefficient: 77×10$^7$/K) by firing at 93° C. for 2 hours and then at 260° C. for another 2 hours. The membrane complex had an effective membrane length of 28 mm after the bonding.

As Example C6, methanol was produced in the same manner as in Example C1, except that the catalyst amount was changed to 30 g, and the flow rate of the circulated raw material gas was changed to 321 mL/min. The methanol partial pressure in the reactor was 0.32 MPaA.

TABLE 4

| | Type of bonding material | Main component of bonding material | Linear expansion coefficient of bonding material upon curing (K$^{-1}$) | Reaction pressure (MPaG) | Raw material gas composition (% by mol) | | | COx conversion rate/ Equibrium COx conversion rate |
|---|---|---|---|---|---|---|---|---|
| | | | | | H$_2$ | CO | CO$_2$ | |
| Example C1 | Low melting point inorganic glass | Bi$_2$O$_3$, B$_2$O$_3$ | 74 × 10$^{-7}$ | 3 | 67 | 33 | 0 | 1.5 |
| Example C2 | Low melting point inorganic glass | Bi$_2$O$_3$, B$_2$O$_3$ | 74 × 10$^{-7}$ | 1.5 | 67 | 33 | 0 | 1.3 |
| Example C3 | Low melting point inorganic glass | Bi$_2$O$_3$, B$_2$O$_3$ | 74 × 10$^7$ | 3 | 67 | 33 | 0 | 1.7 |
| Example C4 | Low melting point inorganic glass | SnO, P$_2$O$_5$ | 63 × 10$^{-7}$ | 3 | 69 | 23 | 7 | 2.5 |
| Example C5 | Low melting point inorganic glass | SnO, P$_2$O$_5$ | 63 × 10$^{-7}$ | 3 | 75 | 0 | 25 | 5.6 |
| Example C6 | Inorganic adhesive | Al$_2$O$_3$ | 77 × 10$^{-7}$ | 3 | 67 | 33 | 0 | 1.3 |

In Table 4, it is seen that, in all of Example Cs, the methanol synthesis reaction proceeded further than the equilibrium as the value of CO$_x$ conversion rate/equilibrium CO$_x$ conversion rate was larger than 1. That is, according to the present invention, methanol can be efficiently produced at a conversion rate higher than the equilibrium conversion rate.

Reference Example C1

A durability test was conducted for O-rings often used for mechanical sealing as bonding materials. As the O-rings, KALREZ (registered trademark) 6375, 7075, 0090, and 7090 were used. The durability test was conducted by enclosing 5 mL of methanol, 5 mL of water, and each bonding material in 70-mL high-pressure container made of SUS316 or HASTELLOY, purging the container with N$_2$, and then heating the container at 250° C. for a prescribed time.

After the test, the durability of each KALREZ (registered trademark) was evaluated by a hardness test (JIS K6253-2: 2012). KALREZ (registered trademark) 6375 and 0090 were observed with a reduction in hardness over time; therefore, they were judged to be not usable under a high temperature and a high pressure in the presence of methanol vapor. Further, KALREZ (registered trademark) 7075 and 7090 were markedly deformed during the test, and the hardness test could not be conducted; therefore, they were also judged to be not usable under a high temperature and a high pressure in the presence of methanol vapor.

Reference Example C2

A durability test was conducted for graphite packings often used for mechanical sealing as bonding materials. As the graphite packings, TOMBO No. 2200-P and No. 2250 manufactured by NICHIAS Corporation were used. The durability test was conducted in the same manner as in Reference Example C1.

After the test, peeling was observed between the graphite packings; therefore, they were judged to be not usable under a high temperature and a high pressure in the presence of methanol vapor.

Reference Example C3

A durability test was conducted for AREMCO-BOND 631, which is a high-vacuum epoxy adhesive used as a bonding material. The durability test was conducted in the same manner as in Reference Example C1, using a sample obtained by bonding an alumina plate and a porous alumina with AREMCO-BOND 631.

After the test, the bonded alumina plate and porous alumina were detached from each other; therefore, AREMCO-BOND 631 was judged to be not usable under a high temperature and a high pressure in the presence of methanol vapor.

As described above, the bonding methods shown in Reference Examples were judged to be not usable under a high temperature and a high pressure in the presence of methanol vapor and, therefore, could not be used for the production of methanol.

The fifth embodiment of the present invention will now be described more concretely; however, needless to say, the scope of the present invention is not limited to the modes shown in the following Examples.

Example D1

Figure 8:
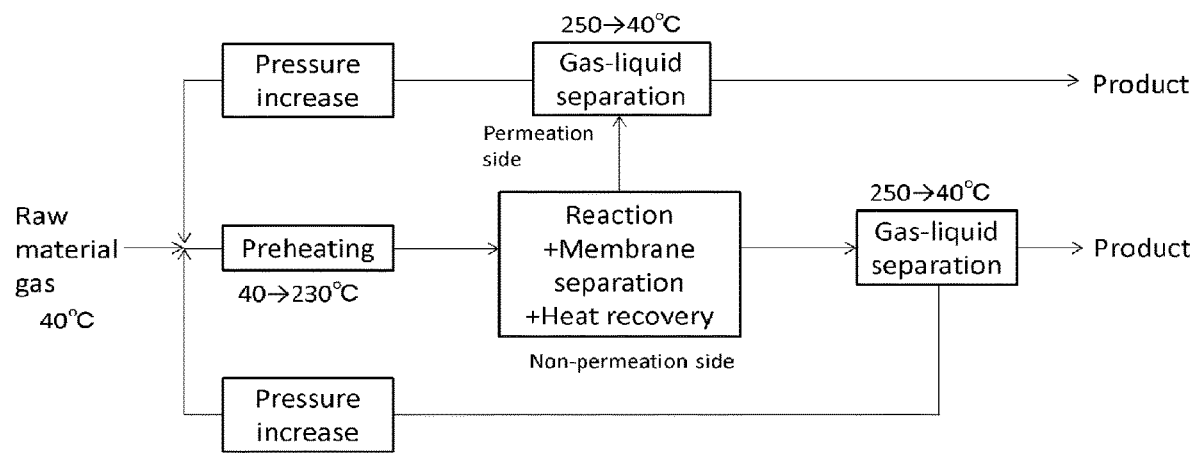
FIG. 8 is a flow chart showing the outline of a production process according to one embodiment of the present invention.

Taking a process of synthesizing methanol from a mixed gas of hydrogen, carbon monoxide and carbon dioxide as an example, a simulation of the process having the general flow shown in FIG. 8 was performed. For this simulation, ASPEN Plus V8.4 and ASPEN Custom Modeler V8.4 manufactured by Aspen Technology Inc. were used. The process conditions were assumed to be as follows.
Raw material gas temperature: 40° C.
Raw material gas preheating temperature: 230° C.
Reaction temperature: 250° C.
Pressure (non-permeation side): 5 MPaG
Pressure (permeation side): 0.1 MPaG
Raw material gas: a mixed gas of $H_2$ and $CO_2$, 100 kmol/hr, having a composition satisfying a relationship of "$H_2$ flow rate=2×CO flow rate+3×$CO_2$ flow rate" based on the stoichiometry of the methanol synthesis reaction after merging with a recycled gas
Catalyst amount: 2,000 kg
Membrane area per unit catalyst volume: 37.5 $m^2/m^3$
It was assumed that the following three equilibrium reactions would occur in the reactor.

$$3H_2+CO_2 \rightarrow CH_3OH+H_2O \quad \text{Formula 1}$$

$$2H_2+CO \rightarrow CH_3OH \quad \text{Formula 2}$$

$$CO_2+H_2 \rightarrow CO+H_2O \quad \text{Formula 3}$$

As reaction rate equations of the respective Formulae, the following equations were used referring to Non-patent Documents 1 and 2.
Reaction rate equation of Formula 1:

$$r_1 = k_1 p_{CO_2}^{0.5} p_{H_2}^{1.5}\left[1 - \frac{p_{CH_3OH} p_{H_2O}}{K_1 P_{CO_2} P_{H_2}^3}\right],$$

$$k_1 = 8.893 \times 10^{-3} \exp(-6163/T),$$

$$K_1(\text{bar}^{-2}) = \exp(-24.6225 + 7221.83/T)$$

Reaction rate equation of Formula 2:

$$r_2 = k_2 p_{CO}^{0.5} p_{H_2}\left[1 - \frac{p_{CH_3OH}}{K_2 P_{CO} P_{H_2}^2}\right],$$

$$k_2 = 0.2032 \times \exp(-2954/T),$$

$$K_2(\text{bar}^{-2}) = \exp(-28.9762 + 11815/T)$$

Reaction rate equation of Formula 3:

$$r_3 = \frac{k_3 p_{CO_2}(1 - K_3(p_{H_2O} p_{CO}/p_{CO_2} p_{H_2}))}{1 + k_4 p_{H_2O}/p_{H_2} + k_5 \sqrt{p_{H_2}} + k_6 p_{H_2O}}$$

$$k_3(\text{mol/kg s bar}) = 1.22 \times 10^{10} \exp(-94765/RT),$$

$$k_4 = 3453.38, k_5(\text{bar}^{0.5}) = 0.499\exp(17197/RT),$$

$$k_5(\text{bar}^1) = 6.62 \times 10^{11}\exp(124119/RT), K_3 = 10^{(2073/T\;2.029)}$$

The following values were used for the performance of separation membrane.
Permeability coefficient of MeOH and $H_2O$: $1.0 \times 10^{-6}$ mol/$m^2 \cdot s \cdot Pa$
Permeability coefficient of components other than MeOH and $H_2O$: $1.0 \times 10^{-8}$ mol/$m^2 \cdot s \cdot Pa$
By the process simulation, the one-path conversion rate and the heat recovery amount were determined. The conversion rate was calculated by the following Formula 5 using the molar flow rates of CO and $CO_2$ at an inlet and an outlet of the reactor (sum of the non-permeation side and the permeation side). The heat recovery amount was defined as the amount of heat required to be removed for maintaining the reactor temperature at 250° C.

Conversion rate (%)=100−(outlet CO molar flow rate+outlet $CO_2$ molar flow rate)/(inlet CO molar flow rate+inlet $CO_2$ molar flow rate)×100  Formula 5

Example D2

Figure 10:
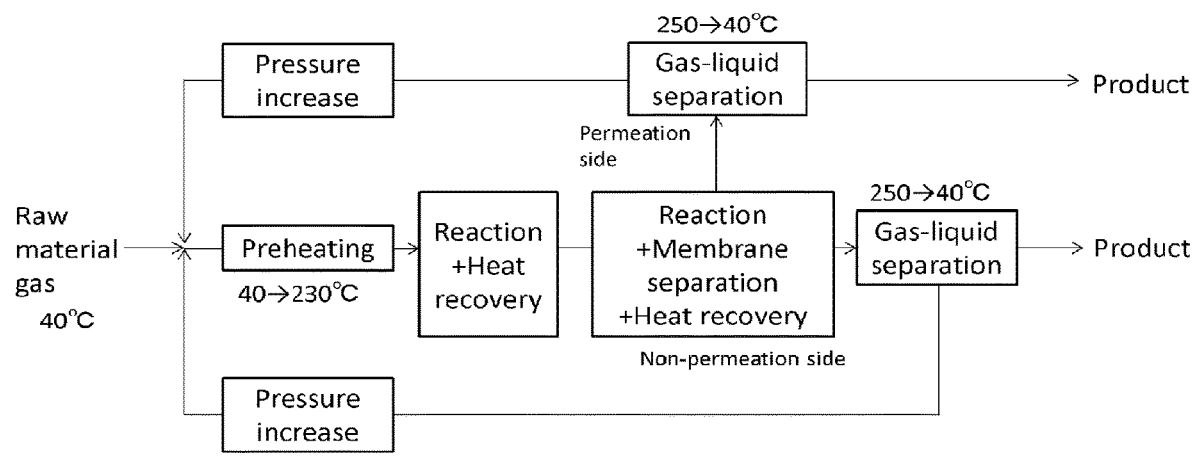
FIG. 10 is a flow chart showing the outline of a production process according to another embodiment of the present invention.

The conversion rate and the heat recovery amount were determined by the same simulation as in Example D1, except that, as shown in FIG. 10, a process of carrying out only the reaction and the heat recovery in a first reactor, and concurrently carrying out the reaction, the membrane separation and the heat recovery in a second reactor was employed. It is noted here that the total amount of the catalyst was set to the same as in Example 1, and the catalyst was equally divided into the two reactors. Further, the membrane area was also the same as in Example D1, based on the total catalyst volume.

Comparative Example D1

Figure 11:
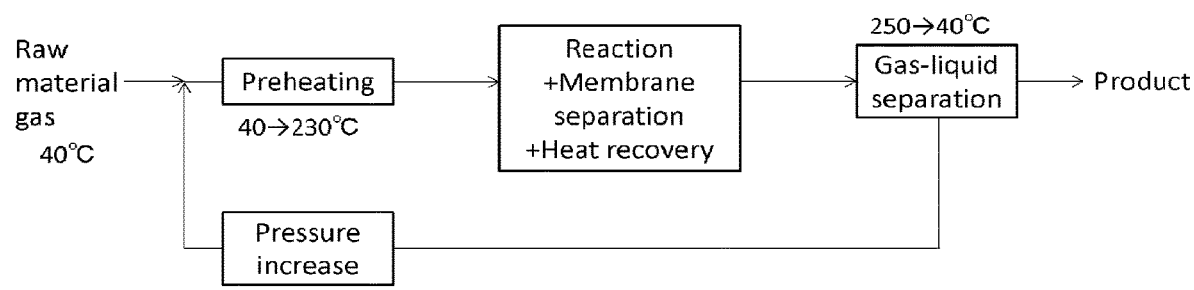
FIG. 11 is a flow chart showing the outline of a production process according to one mode of Comparative Example.

The conversion rate and the heat recovery amount were determined by the same simulation as in Example D1, except that, as shown in FIG. 11, a process of carrying out only the reaction and the heat recovery in a reactor (membrane area per unit catalyst volume was 0 $m^2/m^3$) was employed to eliminate the flow on the permeation side.

Comparative Example D2

Figure 12:
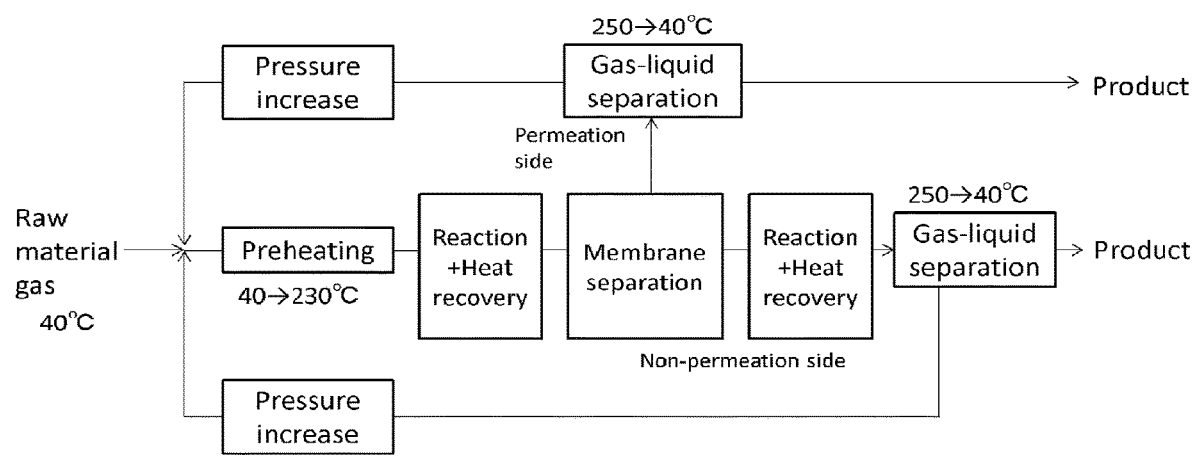
FIG. 12 is a flow chart showing the outline of a production process according to another mode of Comparative Example.

The conversion rate and the heat recovery amount were determined by the same simulation as in Example D1, except that, as shown in FIG. 12, a process of carrying out the reaction and the heat recovery in a first reactor, carrying out only the membrane separation in a second reactor, and carrying out only the reaction and the heat recovery in a third reactor was employed. It is noted here that the total amount of the catalyst was the same as in Example D1, and the catalyst was equally divided into the first and the third reactors. Further, based on the total catalyst volume, the same membrane area as in Example D1 was provided in the second reactor.

As shown in Table D1, the results indicate that the conversion rate was high and the amount of recovered heat was large in those processes where reaction, membrane separation and heat recovery were carried out concurrently.

TABLE 5

Table D1

|  | Conversion rate % | Heat recovery amount GJ/h |
|---|---|---|
| Example D1 | 94 | 1.55 |
| Example D2 | 81 | 1.39 |
| Comparative Example D1 | 25 | 0.32 |
| Comparative Example D2 | 52 | 0.49 |

Reference Example D1

The reactor temperature was estimated assuming that, in FIG. 8, the same process as in Example was employed except that the heat recovery was not carried out and that the reaction heat was used for increasing the temperature of a catalyst layer. However, the reactor temperature was not stabilized even after it exceeded the heat resistant temperature of the membrane.

Example D3

The conversion rate was determined by the same simulation as in Example D1, except that the pressure (non-permeation side) was changed to 3 MPaG, the raw material gas composition was changed to $H_2/CO=2/1$, and the raw material gas flow rate was changed to 75 kmol/hr.

Example D4

The conversion rate was determined by the same simulation as in Example D3, except that the permeability coefficient of the components other than MeOH and $H_2O$ was changed to $5.0 \times 10^{-8}$ mol/$m^2 \cdot s \cdot Pa$.

Example D5

The conversion rate was determined by the same simulation as in Example D3, except that the permeability coefficient of the components other than MeOH and $H_2O$ was changed to $1.0 \times 10^{-7}$ mol/$m^2 \cdot s \cdot Pa$.

Comparative Example D3

The conversion rate was determined by the same simulation as in Example D3, except that the membrane area per unit catalyst volume was changed to 0 $m^2/m^3$, assuming a process not using a separation membrane.

As shown in Table D2, the results indicate that, regardless of the permeability coefficient ratio, a higher conversion rate was obtained in those cases where a separation membrane was used than in those cases where a separation membrane was not used.

TABLE 6

Table D2

|  | Membrane performance (Permeability coefficient of MeOH and H2O)/(Permeability coefficient of other components) | Conversion rate % |
|---|---|---|
| Example D3 | 100 | 96 |
| Example D4 | 50 | 93 |
| Example D5 | 10 | 73 |
| Comparative Example D3 | (No membrane) | 31 |

Example D6

Figure 13:
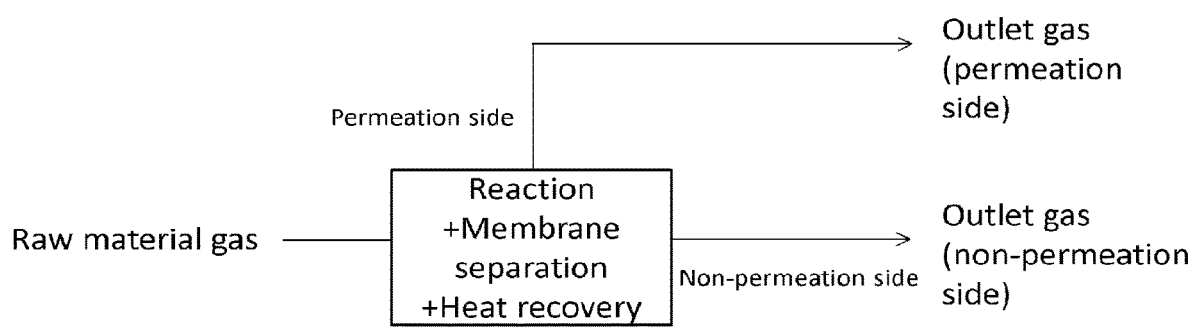
FIG. 13 is a flow chart showing the outline of a production process according to yet another embodiment of the present invention.

A process without recycling, whose general flow is shown in FIG. 13, was simulated. The process conditions were assumed to be as follows.

Reaction temperature: 250° C.
Pressure (non-permeation side): 5 MPaG
Pressure (permeation side): 0.1 MPaG
Raw material gas: $H_2/CO_2=3/1$, flow rate=100 kmol/hr
Catalyst amount: 2,000 kg
Membrane area per unit catalyst volume: 20 $m^2/m^3$ The assumed reactions and reaction rate equations as well as the values of the separation membrane performance were the same as in Example D1, and the conversion rate was determined by the simulation.

Example D7

The conversion rate was determined by the same simulation as in Example D6, except that the reaction temperature was changed to 210° C.

Example D8

The conversion rate was determined by the same simulation as in Example D6, except that the reaction temperature was changed to 230° C.

Example D9

The conversion rate was determined by the same simulation as in Example D6, except that the reaction temperature was changed to 270° C.

Example D10

The conversion rate was determined by the same simulation as in Example D6, except that the reaction temperature was changed to 290° C.

Comparative Example D4

The conversion rate was determined by the same simulation as in Example D6, except that the membrane area per unit catalyst volume was changed to 0 m²/m³, assuming a process not using a separation membrane.

Comparative Example D5

The conversion rate was determined by the same simulation as in Example D7, except that the membrane area per unit catalyst volume was changed to 0 m²/m³, assuming a process not using a separation membrane.

Comparative Example D6

The conversion rate was determined by the same simulation as in Example D8, except that the membrane area per unit catalyst volume was changed to 0 m²/m³, assuming a process not using a separation membrane.

Comparative Example D7

The conversion rate was determined by the same simulation as in Example D9, except that the membrane area per unit catalyst volume was changed to 0 m²/m³, assuming a process not using a separation membrane.

Comparative Example D8

The conversion rate was determined by the same simulation as in Example D10, except that the membrane area per unit catalyst volume was changed to 0 m²/m³, assuming a process not using a separation membrane.

As shown in Table D3, the results indicate that, regardless of the temperature, a higher conversion rate was obtained in those cases where a separation membrane was used than in those cases where a separation membrane was not used.

TABLE 7

Table D3

| | Reaction temperature | Presence or absence of membrane | Conversion rate % |
|---|---|---|---|
| Example D6 | 250 | present | 82 |
| Example D7 | 210 | present | 58 |
| Example D8 | 230 | present | 83 |
| Example D9 | 270 | present | 69 |
| Example D10 | 290 | present | 52 |
| Comparative Example D4 | 250 | absent | 17 |
| Comparative Example D5 | 210 | absent | 25 |
| Comparative Example D6 | 230 | absent | 21 |
| Comparative Example D7 | 270 | absent | 11 |
| Comparative Example D8 | 290 | absent | 8 |

Example D11

The conversion rate was determined by the same simulation as in Example D6, except that the membrane area per unit catalyst volume was changed to 5 m²/m³.

Example D12

The conversion rate was determined by the same simulation as in Example D6, except that the membrane area per unit catalyst volume was changed to 10 m²/m³.

Example D13

The conversion rate was determined by the same simulation as in Example D6, except that the membrane area per unit catalyst volume was changed to 50 m²/m³, and the catalyst amount was changed to 1,000 kg.

As shown in Table D4, the results indicate that, regardless of the membrane area per unit catalyst volume, a higher conversion rate was obtained in those cases where a separation membrane was used than in those cases where a separation membrane was not used.

TABLE 8

Table D4

| | Membrane area per unit catalyst volume m²/m³ | Amount of catalyst kg | Conversion rate % |
|---|---|---|---|
| Example D6 | 20 | 2000 | 82 |
| Example D11 | 5 | 2000 | 34 |
| Example D12 | 10 | 2000 | 50 |
| Example D13 | 50 | 1000 | 80 |
| Comparative Example D4 | 0 | 2000 | 17 |

DESCRIPTION OF SYMBOLS

1: complex of zeolite and inorganic porous support
2: cap
3: dense member (pipe)
4: bonding material
10: reactor
11: flange made of dense member
13: catalyst
101: heat exchanger

The invention claimed is:

1. A bonded body, comprising:
  a dense member;
  a complex of a zeolite and an inorganic porous support; and
  a lead-free inorganic glass bonding the dense member and the complex,
  wherein the lead-free inorganic glass has a thermal expansion coefficient measured at 30 to 250° C. of $30 \times 10^{-7}$/K or more and $90 \times 10^{-7}$/K or less, and a softening point of 397° C. or lower.

2. A bonded body, comprising:
  a dense member;
  a complex of a zeolite and an inorganic porous support; and
  an inorganic glass bonding the dense member and the complex,
  wherein the dense member is a metal member, and the inorganic glass has a thermal expansion coefficient measured at 30 to 250° C. of $30 \times 10^{-7}$/K or more and $90 \times 10^{-7}$/K or less, and a softening point of 397° C. or lower.

3. The bonded body according to claim 1, wherein the inorganic glass comprises $SnO$ and/or $B_2O_3$.

4. A bonded body, comprising:
a dense member;
a complex of a zeolite and an inorganic porous support; and
an inorganic adhesive bonding the dense member and the complex and having a post-curing thermal expansion coefficient of $30 \times 10^{-7}$/K to $90 \times 10^{-7}$/K,
wherein the post-curing thermal expansion coefficient is an average value at 30 to 300° C. and the inorganic adhesive is solidified by a chemical reaction and adheres to the zeolite, inorganic porous support and dense member and is non-invertible to an original state when heated.

5. A bonded body, comprising:
a dense member;
a complex of a zeolite and an inorganic porous support; and
an inorganic adhesive bonding the dense member and the complex,
wherein a difference in thermal expansion coefficient between the dense member and the inorganic adhesive after cured is $50 \times 10^{-7}$/K or less, the after cured thermal expansion coefficient is an average value at 30 to 300° C., and the inorganic adhesive is solidified by a chemical reaction and adheres to the zeolite, inorganic porous support and dense member and is non-invertible to an original state when heated.

6. The bonded body according to claim 4, wherein the inorganic adhesive comprises a metal alkoxide.

7. The bonded body according to claim 1, wherein a bonded part between the complex and the dense member is covered with a sealing film.

8. The bonded body according to claim 7, wherein the sealing film is a silica film.

9. The bonded body according to claim 1, wherein the dense member has a thermal expansion coefficient measured at 30 to 250° C. of $30 \times 10^{-7}$/K or more and $200 \times 10^{-7}$/K or less.

10. A method of using a bonded body, in which the bonded body according to claim 1 is used under a high-temperature condition of 100° C. to 500° C. and/or a high-pressure condition of 0.5 to 10 MPa.

11. A separation membrane module, comprising the bonded body according to claim 1.

12. A reactor, comprising the separation membrane module according to claim 11.

13. A bonding method for bonding a complex of a zeolite and an inorganic porous support to a dense member, comprising:
bonding a complex of a zeolite and an inorganic porous support to a dense member with a lead-free inorganic glass,
wherein the lead-free inorganic glass has a thermal expansion coefficient measured at 30 to 250° C. of $30 \times 10^{-7}$/K or more and $90 \times 10^{-7}$/K or less, and a softening point of 397° C. or lower.

14. A bonding method for bonding a complex of a zeolite and an inorganic porous support to a dense member, comprising:
bonding a complex of a zeolite and an inorganic porous support to a dense member with an inorganic glass,
wherein the dense member is a metal member, and the inorganic glass has a thermal expansion coefficient measured at 30 to 250° C. of $30 \times 10^{-7}$/K or more and $90 \times 10^{-7}$/K or less, and a softening point of 397° C. or lower.

15. The bonded body according to claim 1, wherein the lead-free inorganic glass has a softening point of 357° C. or lower.

* * * * *